(12) United States Patent
Mohammadi et al.

(10) Patent No.: US 9,387,161 B2
(45) Date of Patent: Jul. 12, 2016

(54) METHOD AND COMPOSITIONS FOR REDUCING PORE SIZE, AND MOISTURIZING AND/OR BLURRING APPEARANCE OF DEFECTS ON KERATIN SURFACES

(71) Applicants: Fatemeh Mohammadi, Hauppauge, NY (US); Lisa Qu, Flushing, NY (US); Tsung-wei Robert Mou, Stony Brook, NY (US); Anna Czarnota, Commack, NY (US)

(72) Inventors: Fatemeh Mohammadi, Hauppauge, NY (US); Lisa Qu, Flushing, NY (US); Tsung-wei Robert Mou, Stony Brook, NY (US); Anna Czarnota, Commack, NY (US)

(73) Assignee: ELC Management, LLC, Melville, NY (US)

( * ) Notice: Subject to any disclaimer, the term of this patent is extended or adjusted under 35 U.S.C. 154(b) by 0 days.

(21) Appl. No.: 13/948,862

(22) Filed: Jul. 23, 2013

(65) Prior Publication Data

US 2014/0193351 A1    Jul. 10, 2014

Related U.S. Application Data

(60) Provisional application No. 61/675,389, filed on Jul. 25, 2012.

(51) Int. Cl.

| | | |
|---|---|---|
| *A61K 8/81* | (2006.01) | |
| *A61K 8/895* | (2006.01) | |
| *A61Q 19/00* | (2006.01) | |
| *A61K 8/97* | (2006.01) | |
| *A61Q 19/06* | (2006.01) | |
| *A61Q 19/08* | (2006.01) | |
| *A61K 8/891* | (2006.01) | |
| *A61Q 5/00* | (2006.01) | |

(52) U.S. Cl.
CPC ............... *A61K 8/895* (2013.01); *A61K 8/8152* (2013.01); *A61K 8/8158* (2013.01); *A61K 8/891* (2013.01); *A61K 8/97* (2013.01); *A61Q 19/00* (2013.01); *A61Q 19/06* (2013.01); *A61Q 19/08* (2013.01); *A61Q 5/00* (2013.01); *A61Q 19/007* (2013.01)

(58) Field of Classification Search
None
See application file for complete search history.

(56) References Cited

U.S. PATENT DOCUMENTS

| | | |
|---|---|---|
| 3,215,724 A | 11/1965 | Strobel et al. |
| 3,439,088 A | 4/1969 | Edman |
| 3,781,417 A | 12/1973 | Welters et al. |
| 3,818,105 A | 6/1974 | Coopersmith et al. |
| 4,677,152 A | 6/1987 | Allen et al. |
| 4,702,844 A | 10/1987 | Blesher et al. |
| 4,803,067 A | 2/1989 | Brunetta et al. |
| 4,970,252 A | 11/1990 | Sakuta et al. |
| 5,118,496 A | 6/1992 | Herstein |
| 5,183,588 A | 2/1993 | Salerno et al. |
| 5,183,589 A | 2/1993 | Brunetta et al. |
| 5,236,986 A | 8/1993 | Sakuta |
| 5,412,004 A | 5/1995 | Tachibana et al. |
| 5,654,362 A | 8/1997 | Schulz, Jr. et al. |
| 5,760,116 A | 6/1998 | Kilgour et al. |
| 5,811,487 A | 9/1998 | Schulz, Jr. et al. |
| 5,833,997 A | 11/1998 | Mahieu et al. |
| 5,837,793 A | 11/1998 | Harashima et al. |
| 5,843,193 A | 12/1998 | Hawkins et al. |
| 5,919,468 A | 7/1999 | Bara |
| 6,093,410 A | 7/2000 | Peffly et al. |
| 6,471,952 B1 | 10/2002 | Dubief et al. |
| 7,687,574 B2 | 3/2010 | Lu et al. |
| 7,833,541 B2 | 11/2010 | Lu et al. |
| 2003/0031692 A1 | 2/2003 | Jager Lezer |
| 2004/0033206 A1 | 2/2004 | Dubief et al. |
| 2004/0265258 A1 | 12/2004 | Robinson et al. |
| 2008/0009600 A1* | 1/2008 | Lu et al. .................. A61K 8/062 528/12 |
| 2008/0145436 A1 | 6/2008 | Lorant |
| 2008/0199418 A1 | 8/2008 | Koroskenyi et al. |
| 2009/0324652 A1 | 12/2009 | Polonka et al. |
| 2010/0203077 A1 | 8/2010 | Schnittger et al. |
| 2011/0123579 A1* | 5/2011 | Mohammadi et al. ........ 424/401 |
| 2014/0336308 A1 | 11/2014 | Mateu et al. |

FOREIGN PATENT DOCUMENTS

| | | |
|---|---|---|
| EP | 1932511 A2 | 6/2008 |
| EP | 1932511 A3 | 1/2009 |
| JP | S6118708 | 1/1986 |
| JP | 2000327516 | 11/2000 |
| JP | 2002-212049 | 7/2002 |
| JP | 2004-210654 | 7/2004 |
| JP | 2008-247769 | 10/2008 |
| JP | 2011-246372 | 12/2011 |
| KR | 10-2007-0121048 | 12/2007 |
| WO | WO-2005/048958 | 6/2005 |
| WO | WO-2006/124538 | 11/2006 |
| WO | WO-2007/130412 | 11/2007 |
| WO | WO-2007/130460 | 11/2007 |
| WO | WO-2009/085472 | 7/2009 |
| WO | WO-2009/156249 | 12/2009 |
| WO | WO-2010/002586 | 1/2010 |
| WO | WO-2010/084055 | 7/2010 |

(Continued)

OTHER PUBLICATIONS

Mintel, "Ultim-Age the Ultimate Anti-Aging Serum", Jan. 2011, pp. 1-6.*

(Continued)

*Primary Examiner* — Brian Gulledge
(74) *Attorney, Agent, or Firm* — Julie Blackburn

(57) ABSTRACT

A method for simultaneously moisturizing and/or blurring the appearance of skin defects, or reducing pore size, or treating skin with a multi-benefit composition.

12 Claims, 2 Drawing Sheets

(56) References Cited

FOREIGN PATENT DOCUMENTS

| WO | WO 2013/142471 | * | 9/2013 | ............... A61K 8/81 |
| WO | WO-2013/142471 | | 9/2013 | |

OTHER PUBLICATIONS

Bernard et al., "A New Polymer with a MAXimum Resistance to Electrolytes", SOFW-Journal, 2010, vol. 136., pp. 55-58.* http://www.gnpd.com; Mintel GNPD; Anti-Cracking Moisture; Record ID 1257054; Shantou Shilulan Cosmetics; Mischief Baby; Skincare; Body Care; China; Jan. 2010.

http://www.gnpd.com; Mintel GNPD; Ultim-Age the Ultimate Anti-Ageing Serum; Record ID 1480536; Immanence-IDS; IDC+; Skincare; Face/Neck Care; France; Jan. 2011.

Amazon website; Filorga TIME-FILLER MAT 50ml; Jan. 23, 2012; http://www.amazon.co.uk/Filorga-TIME-FILLER-MAT-50ml/dp/B00C103Sl; pp. 1 and 2.

Catalog; Dermo-Relaxing Age Defense Brightening Cream (SPF-12); 2007; http://www.lubrizol.com/PersonalCare/F-0067-Dermo-Relaxing-Age-Defense-Brightening-Cream.pdf.

PCT International Search Report; International Application No. PCT/US2013/051712; Completion Date: Oct. 17, 2013; Mailing Date: Oct. 18, 2013.

PCT Written Opinion of the International Searching Authority; International Applicattion No. PCT/US2013/051712; Completion Date: Oct. 17, 2013; Mailing Date: Oct. 18, 2013.

Bernard, et al.; A New Polymer With a Maximum Resistance to Electrolytes; SOFW-Journal, 2010; vol. 135; pp. 55-58.

Sodium Polyacrylate Crosspolymer-1; www.personalcarecouncil.org; On-Line INFOBASE; published on Oct. 11, 2013.

Supplemental European Search Report: EP13822208.8; Mailing Date: Jan. 12, 2016; Completion Date: Dec. 17, 2015.

PCT International Search Report; International Application No. PCT/US2015/042608; Completion Date: Sep. 30, 2015; Mailing Date: Sep. 30, 2015.

PCT Written Opinion of the International Searching Authority; International Application No. PCT/US2015/042608; Completion Date: Sep. 30, 2015; Mailing Date: Sep. 30, 2015.

* cited by examiner

METHOD AND COMPOSITIONS FOR REDUCING PORE SIZE, AND MOISTURIZING AND/OR BLURRING APPEARANCE OF DEFECTS ON KERATIN SURFACES

CROSS-REFERENCE TO RELATED APPLICATIONS

This application claims priority from Provisional U.S. Patent Application Ser. No. 61/675,389 filed Jul. 25, 2012.

TECHNICAL FIELD

The invention is the in the field of methods for reducing pore size, moisturizing and optically improving the appearance of keratin surfaces such as skin, hair, or nails with certain polymers and polymer compositions.

BACKGROUND OF THE INVENTION

There is a need for skin care products that have multiple benefits. Desirable multiple benefits include moisturizing, minimizing or blurring the appearance of skin defects, reducing pore size, improving the appearance of dark under eye circles, reducing skin redness (e.g. due to rosacea), minimizing the appearance of lines and wrinkles, evening skin tone, filling skin depressions, hiding scars, smoothing cellulite or "cottage cheese" skin, reducing the ashy appearance of ethnic skin, irregularities and age spots on hands, face, and neck, improving appearance of uneven pigmentation, correcting color (e.g. reducing yellow or red skin tone) and so on.

For example, in the moisturizer category there are many on the market. However, the aesthetics of those products is not always optimal. For example, products that moisturize well may also be too occlusive and provide a heavy or sticky feel on the skin. This in turn may cause blemishes in those with sensitive skin. Often moisturizers provide a shiny appearance on skin, which in turn accentuates the appearance of skin defects. Thus, skin care products that provide optimal moisturization of skin and are aesthetically pleasing are always in demand.

Another desirable property of skin care products is their ability to improve the appearance of skin defects inherently, that is, preferably without using pigments or powders known for this purpose. One way to blur skin defects is by reducing the gloss in the compositions applied to skin. Skin defects are much more visible on skin that is glossy in appearance, in the same way that scratches are most easily seen on wooden floors varnished with a high gloss finish. Often the ingredients present in a formula that are the best moisturizers tend to be glossy or contribute gloss to the overall composition. Accordingly, there is a need for compositions that provide maximum moisture with minimum gloss.

In addition, products that reduce the size of pores are very desirable to consumers. Pore size reduction can occur by topical application of ingredients that physically act on the pore to reduce its size, or which, through optical properties provide the appearance of reduced pore size.

An object of the invention is to provide compositions that moisturize skin.

Another object of the invention is to provide compositions that have multiple benefits including benefits such moisturizing, minimizing or blurring the appearance of skin defects, reducing pore size, improving the appearance of dark under eye circles, reducing skin redness (e.g. due to rosacea), minimizing lines and wrinkles, evening skin tone, filling skin depressions, hiding scars, smoothing cellulite or "cottage cheese" skin, reducing the ashy appearance of ethnic skin, irregularities and age spots on hands, face, and neck, improving appearance of uneven pigmentation, correcting color (e.g. reducing yellow or red skin tone) and so on.

Another object of the invention is to provide compositions that optically blur the appearance of skin defects such as depressions, irregularities, uneven skin tone, etc. which may be by de-glossing, and which can occur without the use of particulates traditionally used for this purpose.

Another object of the invention is to provide compositions that reduce the appearance of pores.

Another object of the invention is to provide a method for moisturizing and/or blurring or minimizing the appearance of defects on keratinous surfaces such as skin, hair, or nails. Improving the appearance of hands is particularly desired since hands often show age that is less treatable than other areas of the face or body.

SUMMARY OF THE INVENTION

A method for simultaneously moisturizing a keratin surface and/or blurring the appearance of defects, preferably by de-glossing the keratin surface, comprising topically applying to a surface in need of moisturization and/or having such defects, a composition containing a Polymer (as defined below) wherein the composition containing the Polymer exhibits improved moisturization and de-glossing when compared to the same composition not containing the Polymer. (The term "Polymer" is a defined term having the definition set forth below in Section II below).

A method for optically blurring the appearance of defects on a keratin surface preferably by de-glossing the keratin surface, by topically applying to a surface having such defects a composition containing a Polymer wherein the composition containing the Polymer exhibits improved efficacy in blurring the appearance of such defects when compared to the same composition not containing the Polymer.

A method for reducing the size of pores on skin by topically applying to a skin surface having enlarged pores a composition containing a Polymer wherein the composition containing the Polymer reduces the size of skin pores when compared to the same composition not containing the Polymer.

The invention is also directed to a multi-benefit composition and method for treating skin to provide at least two benefits selected from the group: (a) moisturizing, (b) blurring the appearance of skin defects, (c) reducing pore size, (d) improving the appearance of dark under eye circles, (e) reducing skin redness (e.g. due to rosacea), (f) minimizing the appearance of lines and wrinkles, (g) evening skin tone, (h) filling skin depressions, (i) hiding scars, (j) smoothing cellulite or "cottage cheese" skin, (k) reducing the ashy appearance of ethnic skin, (l) minimizing the appearance of irregularities and age spots on hands, face, and neck, (m) improving appearance of uneven pigmentation, (n) correcting color (e.g. reducing yellow or red skin tone); and combinations thereof by applying a topical composition containing the Polymer.

The invention is also directed to a topical composition comprising the Polymer.

The invention is also directed to a topical composition comprising the Polymer in combination with other ingredients further set forth herein.

DETAILED DESCRIPTION

I. Definitions

Figure 1:
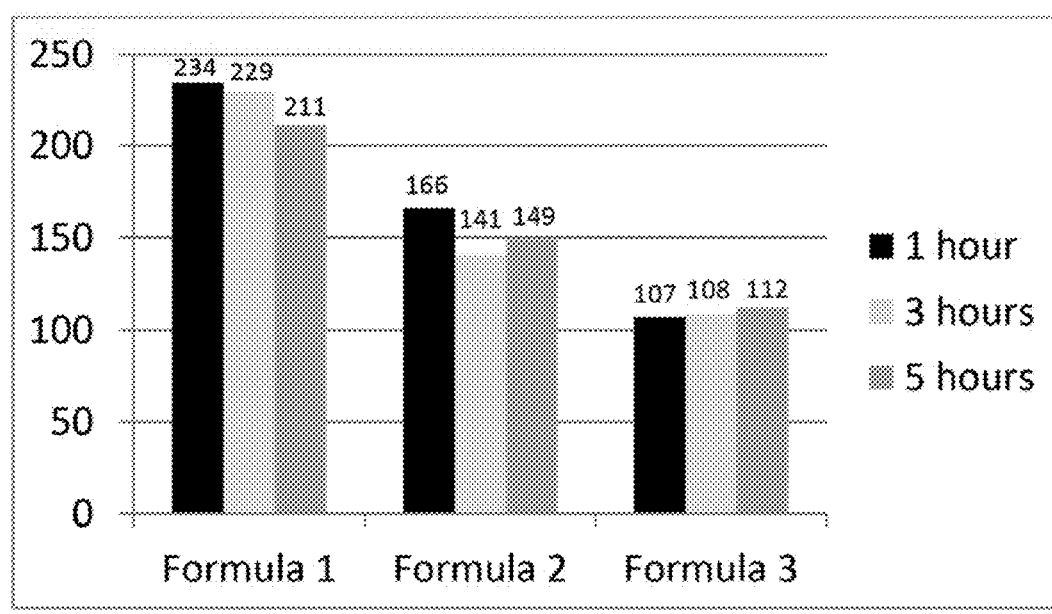
FIG. 1: shows that the composition of the invention (Formula 1) provides improved moisturization when compared to test formulas (2 & 3).

All percentages mentioned herein are percentages by weight unless otherwise indicated.

The term "blur" means, with respect to defects, that such defects are obscured or made less distinct.

The term "defects" means, with respect to skin conditions such as wrinkles, fine lines, large pores, uneven pigmentation, pock marks, pits, scars, or similar superficial irregularities.

The term "de-gloss" means that the measured gloss of the surface is reduced. Typically gloss is measured by a gloss meter including according to methods as set forth in the Examples.

The term "keratin surface" means skin, hair, or nails.

The term "Polymer" means the polymers set forth in Section II, below.

II. The Polymer (the "Polymer")

Suitable polymers are those generally referred to as polyacrylate polymers crosslinked with different crosslinking agents. They are referred to by the C.T.F.A. names as Polyacrylate crosspolymer-1, 2, 3, 4, 5, 6, 7, 8, 9, 10, 11, 12, 13, or 14.

Polyacrylate crosspolymer-1 is a copolymer of one or more simple esters of acrylic or methacrylic acid, C1-4 dialkylamino C1-6 alkyl methacrylate, PEG/PPG-30/5 allyl ether, PEG 20-25 C10-30 alkyl ether methacrylate, hydroxy C2-6 alkyl methacrylate crosslinked with ethylene glycol dimethacrylate. This polymer may be purchased from Lubrizol Advanced Materials under the tradename Carbopol Aqua CC.

Polyacrylate crosspolymer-2 is a copolymer of PEG/PPG-23/6 Dimethicone citraconate. C10-30 alkyl PEG-25 methacrylate, and one or more monomers of acrylic acid, methacrylic acid or one of their simple esters, crosslinked with trimethylolpropane PEG-15 triacrylate. It may be purchased from Lubrizol under the Fixate tradename.

Polyacrylate crosspolymer-3 may also be suitable. It is a copolymer of butyl acrylate, PEG-10 acrylate, PPG-6 acrylate and dimethylacrylamide, crosslinked by PEG-23 Diacrylate and may be purchased from Goo Chemical Company.

Polyacrylate crosspolymer-4 is suitable, and is a copolymer of sodium acryloyldimethyltaurate, dimethyl acrylamide, sodium acrylate, acrylic acid and hydroxyethylacrylate crosslinked with methylene bis-propenamide that may be purchased from Seppic Inc under the tradename Seppinov P500.

Also suitable is Polyacrylate crosspolymer-5, and Polyacrylate crosspolymer-6, which is a copolymer of ammonium acryloyldimethyltaurate, dimethylacrylamide, lauryl methacrylate and laureth-4 methacrylate, crosslinked with trimethylolpropane triacrylate that can be purchased from Seppic Inc.

Also suitable is Polyacrylate crosspolymer-8 a copolymer of t-butyl methacrylate, stearyl methacrylate, methoxy PEG-23 methacrylate, and dimethylacrylamide, crosslinked with ethylene glycol dimethacrylate, and Polyacrylate crosspolymer-9 which is a copolymer of t-butylaminoethyl methacrylate and carboxyethyl acrylate, crosslinked with a combination of pentaerythritol tetraacrylate and a hexafunctional acrylate formed by reacting pentaerythritol triacrylate with toluene diisocyanate.

Polyacrylate crosspolymer-10 and 11 are also suitable, and are copolymers prepared by polymerizing a mixture of trimethoxysilylpropylmethacrylate with trimethyloylpropane trimethacrylate; or copolymers of methacrylic acid, acryloyl dimethyltaurate and dimethacrylamide, crosslinked with ppg-3 glyceryl triacrylate, with the latter optionally neutralized with ammonia, respectively.

Polyacrylate crosspolymer-12 is a copolymer of t-butyl methacrylate, stearyl methacrylate, methoxy PEG-23 methacrylate, and dimethylacrylamide, crosslinked with methylene bis-acrylamide and Polyacrylate crosspolymer-14 is a copolymer of copolymer of acrylic acid, lauryl methacrylate, cetyl methacrylate, stearyl methacrylate, and phosphorylcholine glycol methacrylate, crosslinked by an allyl ether of pentaerythritol.

One particularly preferred polymer that may be used in the composition of the invention contains silicone and acrylate repeat units. More specifically the preferred polymer is a copolymer of acrylates and silicone and contains polyether repeat units and crosslinked epoxy or oxirane repeat units. The polymer may be present in the composition in amount ranging from about 0.01 to 75%, preferably from about 0.05 to 60%, more preferably from about 0.1 to 50% by weight of the total composition. Suitable polymers are disclosed in U.S. Pat. Nos. 7,833,541 and 7,687,574, both of which are hereby incorporated by reference in their entirety. The silicone copolymer is preferably made by reacting an organosiloxane silyl hydride polymer with an olefinic polyether and oxirane or epoxy groups by hydrosilation, then crosslinking with acrylates. The term "acrylate" is used generically to refer to any unit that contains acrylic acid, methacrylic acid or their simple esters. More specifically, the polymer used in the composition of the invention is the reaction product of a silyl hydride copolymer with an olefinic polyether under hydrosilylation conditions to yield a polyether substituted hydride terpolymer.

In one embodiment the copolymer may be the reaction product of:

a) $M_a M^H_{b-h-k} M^{PE}_h M^E_k D_c D^H_{d-i-l} D^{PE}_i D^E_l T_e T^H_{f-j-m} T^{PE}_j T^E_m Q_g$; and b) a stoichiometric or super-stoichiometric quantity of acrylate where $M = R^1 R^2 R^3 SiO_{1/2}$;

$M^H = R^4 R^5 HSiO_{1/2}$;

$M^{PE} = R^4 R^5 (-CH_2 CH(R^9)(R^{10})_n O(R^{11})_o (C_2 H_4 O)_p (C_3 H_6 O)_q (C_4 H_8 O)_r - R^{12}) SiO_{1/2}$;

$M^E = R^4 R^5 (-R^{17} R^{18} C - CR^{16} Q_s Q_t R^{15}(COC) R^{13} R^{14}) SiO_{1/2}$;

$D = R^6 R^7 SiO_{2/2}$; and $D^H = R^8 HSiO_{2/2}$, $D^{PE} = R^8 (-C_2 CH(R^9)(R^{10})_n O(R^{11})_o (C_2 H_4 O)_p (C_3 H_6 O)_q (C_4 H_8 O) R^{12}) SiO_{2/2}$;

$D^E = R^8 (-R^{17} R^{18} C - CR^{16} Q_s Q_t R^{15}(COC) R^{13} R^{14}) SiO_{2/2}$;

$T^H = HSiO_{3/2}$;

$T^{PE} = (-CH_2 CH(R^9)(R^{10})_n O(R^{11})_o (C_2 H_4 O)_p (C_3 H_6 O)_q (C^4 H^8 O)_r R^{12}) SiO_{3/2}$;

$T^E = (-R^{17} R^{18} C - CR^{16} Q_s Q_t R^{15}(COC) R^{13} R^{14}) SiO_{3/2}$; and $Q = SiO_{4/2}$;

where $R^1$, $R^2$, $R^3$, $R^4$, $R^5$, $R^6$, $R^7$, $R^8$ and $R^{19}$ are each independently selected from the group of monovalent hydrocarbon radicals having from 1 to 60 carbon atoms;

$R^9$ is H or a 1 to 6 carbon atom alkyl group; $R^{10}$ is a divalent alkyl radical of 1 to 6 carbons;

$R^{11}$ is selected from the group of divalent radicals consisting of —$C_2H_4O$—, —$C_3H_6O$—, and —$C_4H_8O$; $R^{12}$ is H, a monofunctional hydrocarbon radical of 1 to 6 carbons, or acetyl; $R^{13}$, $R^{14}$, $R^{15}$, $R^{16}$, $R^{17}$ and $R^{18}$ are each independently selected from the group of hydrogen and monovalent hydrocarbon radicals having from one to sixty carbon atoms, $Q_t$ is a di- or trivalent hydrocarbon radical having from one to sixty carbon atoms, $Q_s$ is a divalent hydrocarbon radical having from one to sixty carbon atoms; and the subscripts a, b, or c is positive and has a value ranging from about 5 to about 1,000;

the subscript d is positive and has a value ranging from about 3 to about 400;

the subscript e is zero or positive and has a value ranging from 0 to about 50;

the subscript f is zero or positive and has a value ranging from 0 to about 30;

the subscript g is zero or positive and has a value ranging from 0 to about 20;

the subscript h is zero or positive and has a value ranging from 0 to about 2;

the subscript i is zero or positive and has a value ranging from 0 to about 200;

the subscript j is zero or positive and has a value ranging from 0 to about 30;

the subscript k is zero or positive and has a value ranging from 0 to about 2;

the subscript l is zero or positive and has a value ranging from 0 to about 200;

the subscript m is zero or positive and has a value ranging from 0 to about 30;

the subscript n is zero or one;

the subscript o is zero or one;

the subscript p is zero or positive and has a value ranging from 0 to about 100 subject to the limitation that (p+q+r)>0;

the subscript q is zero or positive and has a value ranging from 0 to about 100 subject to the limitation that (p+q+r)>0;

the subscript r is zero or positive and has a value ranging from 0 to about 100 subject to the limitation that (p+q+r)>0;

the subscript s is zero or one;

the subscript t is zero or one; and c) a free radical initiator.

Thus in one specific embodiment, the process of the invention leading to compositions of the invention is as follows, a silyl hydride having the formula:

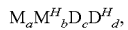

where
$M = R^1R^2R^3SiO_{1/2}$;
$M^H = R^4R^5HSiO_{1/2}$;
$D = R^6R^7SiO_{2/2}$; and
$D^H = R^8HSiO_{2/2}$
with $R^1$, $R^2$, $R^3$, $R^4$, $R^5$, $R^6$, $R^7$, $R^8$ and $R^{19}$ are each independently selected from the group of monovalent hydrocarbon radicals having from 1 to 60 carbon atoms, where the subscripts a, b, c and d are zero or positive; and then is reacted under hydrosilylation conditions with olefinic polyether having the formula:

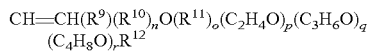

where
$R^9$ is H or a 1 to 6 carbon atom alkyl group;
$R^{10}$ is a divalent alkyl radical of 1 to 6 carbons where the subscript n may be 0 or 1;
$R^{11}$ is selected from the group of divalent radicals consisting of —$C_2H_4O$—, —$C_3H_6O$—, and —$C_4H_8O$— where the subscript o may be 0 or 1;
$R^{12}$ is H, a monofunctional hydrocarbon radical of 1 to 6 carbons, or acetyl and the subscripts p, q and r are zero or positive.

When the polyether is composed of mixed oxyalkyleneoxide groups such as oxyethylene, oxypropylene and oxybutylene, the units may be blocked, or randomly distributed. The resulting terpolymer has a formula consistent with the formula:

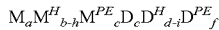

where the superscript PE indicates polyether substitution, with
$M^{PE} = R^4R^5(—CH_2CH(R^9)(R^{10})_nO(R_{11})_o(C_2H_4O)_p (C_3H_6O)_q(C_4H_8O)_rR^{12})SiO_{1/2}$ and
$D^{PE} = R_8(—CH_2CH(R^9)(R^{10})_nO(R^{11})_o(C_2H_4O)_p(C_3H_6O)_q (C_4H_8O)_rR_y^{12})SiO_{2/2}$ This terpolymer may be further reacted under hydrosilylation conditions with a of an olefinic epoxide or oxirane having the formula:

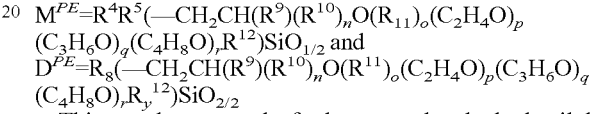

wherein:

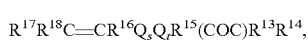

where $R^{13}$, $R^{14}$, $R^{15}$, $R^{16}$, $R^{17}$ and $R^{18}$ are each independently selected from the group of hydrogen and monovalent hydrocarbon radicals having from one to sixty carbon atoms, $Q_t$ is a di- or trivalent hydrocarbon radical having from one to sixty carbon atoms, $Q_s$ is a divalent hydrocarbon radical having from one to sixty carbon atoms with the subscripts s and t independently zero.

The resulting polymer has a formula consistent with:
$M_aM^H_{b-h-k}M_c^{PE}M^E_gD_cD^H_{d-i-l}D^{PE}_fD^E_j$, where the superscript E indicates epoxide or oxirane substitution, with
$ME = R^4R^5(—R^{17}R^{18}C—CR^{16}Q_sQ_tR^{15}(COC)R^{13}R^{14}) SiO_{1/2}$
$D^E = R^8(—R^{17}R^{18}—CR^{16}Q_sQ_tR^{15}(COC)R^{13}R^{14})SiO_{2/2}$ Most preferred is Polyacrylate crosspolymer-7 which is a copolymer of methacrylate PPG-6 phosphate and one or more monomers of acrylic acid, methacrylic acid or their simple esters crosslinked with dimethicone PEG/PPG-25/29 acrylate.

III. Other Moisturizing Ingredients

The composition may contain other moisturizing ingredients or ingredients that provide skin benefits. Preferably such optional additional ingredients are included in an amount sufficient to increase the moisturizing effect (if moisturizing ingredients) of the applied composition without affecting or decreasing the de-glossing effect. If present, suggested ranges of the additional moisturizing ingredient are from about 0.01 to 50%, preferably from about 0.05 to 40%, more preferably from about 0.1 to 35%. The moisturizing ingredient may act by supplementing the water content of the keratin surface or by providing a protective or occlusive layer on the keratin surface to prevent water that is inherently present there from evaporating from the surface.

Polysaccharides may be suitable moisturizers. Examples include naturally derived materials such as agar, agarose, algin, alginic acid, *acacia* gum, amylopectin, chitin, dextran, cassia gum, cellulose gum, gelatin, gellan gum, hyaluronic acid, hydroxyethyl cellulose, methyl cellulose, ethyl cellulose, pectin, sclerotium gum, xanthan gum, pectin, trehelose, gelatin, *Alicaligenes polysaccharides*, hydroxypropyl methylcellulose, amodimethicone, and so on.

Examples of suitable moisturizers further include glycols, sugars, and the like. Suitable glycols are in monomeric or polymeric form and include polyethylene and polypropylene glycols such as PEG 4-200, which are polyethylene glycols having from 4 to 200 repeating ethylene oxide units; as well as $C_{1-6}$ alkylene glycols such as propylene glycol, butylene glycol, pentylene glycol, glycerin and the like. Suitable sugars, some of which are also polyhydric alcohols, are also suitable humectants. Examples of such sugars include glucose, fructose, honey, hydrogenated honey, inositol, maltose, mannitol, maltitol, sorbitol, sucrose, xylitol, xylose, and so on.

Also suitable is urea or hydroxyl $C_{1-4}$alkyl derivatives thereof such as hydroxyethyl urea. Various oily ingredients may also be suitable moisturizers including but not limited to mono-, di-, or triesters of carboxylic acids and aliphatic or aromatic alcohols. Examples include those set forth in Example 1.

IV. Other-Glossing Ingredients

It may also be desirable to include de-glossing ingredients. Preferably the de-glossing ingredients are present in an amount sufficient to increase the de-glossing effect of the topically applied composition and without negatively affecting moisturization. If present such additional de-glossing ingredients may range from about 0.01 to 60%, preferably from about 0.05 to 50%, more preferably from about 0.1 to 45%.

Silicone elastomers that are suitable de-glossing ingredients for use in the compositions of the invention include those that are formed by addition reaction-curing, by reacting an SiH-containing diorganosiloxane and an organopolysiloxane having terminal olefinic unsaturation, or an alpha-omega diene hydrocarbon, in the presence of a platinum metal catalyst. Such elastomers may also be formed by other reaction methods such as condensation-curing organopolysiloxane compositions in the presence of an organotin compound via a dehydrogenation reaction between hydroxyl-terminated diorganopolysiloxane and SiH-containing diorganopolysiloxane or alpha omega diene; or by condensation-curing organopolysiloxane compositions in the presence of an organotin compound or a titanate ester using a condensation reaction between an hydroxyl-terminated diorganopolysiloxane and a hydrolysable organosiloxane; peroxide-curing organopolysiloxane compositions which thermally cure in the presence of an organoperoxide catalyst.

One type of elastomer that may be suitable is prepared by addition reaction-curing an organopolysiloxane having at least two lower alkenyl groups in each molecule or an alpha-omega diene; and an organopolysiloxane having at least two silicon-bonded hydrogen atoms in each molecule; and a platinum-type catalyst. While the lower alkenyl groups such as vinyl, can be present at any position in the molecule, terminal olefinic unsaturation on one or both molecular terminals is preferred. The molecular structure of this component may be straight chain, branched straight chain, cyclic, or network. These organopolysiloxanes are exemplified by methylvinylsiloxanes, methylvinylsiloxane-dimethylsiloxane copolymers, dimethylvinylsiloxy-terminated dimethylpolysiloxanes, dimethylvinylsiloxy-terminated dimethylsiloxane-methylphenylsiloxane copolymers, dimethylvinylsiloxy-terminated dimethylsiloxane-diphenylsiloxane-methylvinylsiloxane copolymers, trimethylsiloxy-terminated dimethylsiloxane-methylvinylsiloxane copolymers, trimethylsiloxy-terminated dimethylsiloxane-methylphenylsiloxane-methylvinylsiloxane copolymers, dimethylvinylsiloxy-terminated methyl(3,3,3-trifluoropropyl) polysiloxanes, and dimethylvinylsiloxy-terminated dimethylsiloxane-methyl(3,3,-trifluoropropyl)siloxane copolymers, decadiene, octadiene, heptadiene, hexadiene, pentadiene, or tetradiene, or tridiene.

Curing proceeds by the addition reaction of the silicon-bonded hydrogen atoms in the dimethyl methylhydrogen siloxane, with the siloxane or alpha-omega diene under catalysis using the catalyst mentioned herein. To form a highly crosslinked structure, the methyl hydrogen siloxane must contain at least 2 silicon-bonded hydrogen atoms in each molecule in order to optimize function as a crosslinker.

The catalyst used in the addition reaction of silicon-bonded hydrogen atoms and alkenyl groups, and is concretely exemplified by chloroplatinic acid, possibly dissolved in an alcohol or ketone and this solution optionally aged, chloroplatinic acid-olefin complexes, chloroplatinic acid-alkenylsiloxane complexes, chloroplatinic acid-diketone complexes, platinum black, and carrier-supported platinum.

Examples of suitable silicone elastomers for use in the compositions of the invention may be in the powder form, or dispersed or solubilized in solvents such as volatile or non-volatile silicones, or silicone compatible vehicles such as paraffinic hydrocarbons or esters. Examples of silicone elastomer powders include vinyl dimethicone/methicone silesquioxane crosspolymers like Shin-Etsu's KSP-100, KSP-101, KSP-102, KSP-103, KSP-104, KSP-105, hybrid silicone powders that contain a fluoroalkyl group like Shin-Etsu's KSP-200 which is a fluoro-silicone elastomer, and hybrid silicone powders that contain a phenyl group such as Shin-Etsu's KSP-300, which is a phenyl substituted silicone elastomer; and Dow Corning's DC 9506. Examples of silicone elastomer powders dispersed in a silicone compatible vehicle include dimethicone/vinyl dimethicone crosspolymers supplied by a variety of suppliers including Dow Corning Corporation under the tradenames 9040 or 9041, GE Silicones under the tradename SFE 839, or Shin-Etsu Silicones under the tradenames KSG-15, 16, 18. KSG-15 has the CTFA name cyclopentasiloxane/dimethicone/vinyl dimethicone crosspolymer. KSG-18 has the INCI name phenyl trimethicone/dimethicone/phenyl vinyl dimethicone crosspolymer. Silicone elastomers may also be purchased from Grant Industries under the Gransil trademark. Also suitable are silicone elastomers having long chain alkyl substitutions such as lauryl dimethicone/vinyl dimethicone crosspolymers supplied by Shin Etsu under the tradenames KSG-31, KSG-32, KSG-41, KSG-42, KSG-43, and KSG-44. Cross-linked organopolysiloxane elastomers useful in the present invention and processes for making them are further described in U.S. Pat. No. 4,970,252 to Sakuta et al., issued Nov. 13, 1990; U.S. Pat. No. 5,760,116 to Kilgour et al., issued Jun. 2, 1998; U.S. Pat. No. 5,654,362 to Schulz, Jr. et al. issued Aug. 5, 1997; and Japanese Patent Application JP 61-18708, assigned to Pola Kasei Kogyo K. K, each of which are herein incorporated by reference in its entirety.

Other examples include silicone copolymers referred to under the C.T.F.A. designation "Polysilicone" followed by a numbers 8, 9, 10, 11, 12, 13, 14, 15, 16, 17, 18, 19, 20, 21, 22, 23, 24, 25, 26, or 27.

V. Other Ingredients

A. Botanical Extracts

It may be desirable to include one or more botanical extracts in the compositions. If so, suggested ranges are from about 0.0001 to 10%, preferably about 0.0005 to 8%, more preferably about 0.001 to 5% by weight of the total composition. Suitable botanical extracts include extracts from plants (herbs, roots, flowers, fruits, seeds) such as flowers, fruits, vegetables, and so on, including yeast ferment extract, *Padina Pavonica* extract, *thermus* thermophilis ferment extract, camelina sativa seed oil, *boswellia serrata* extract, olive extract, *Aribodopsis Thaliana* extract, *Acacia Dealbata* extract, *Acer Saccharinum* (sugar maple), acidopholus, acorus, *aesculus, agaricus*, agave, agrimonia, algae, aloe, *citrus, brassica*, cinnamon, orange, apple, blueberry, cranberry, peach, pear, lemon, lime, pea, seaweed, caffeine, green tea, chamomile, willowbark, mulberry, poppy, and those set forth on pages 1646 through 1660 of the CTFA Cosmetic Ingredient Handbook, Eighth Edition, Volume 2. Further specific examples include, but are not limited to, *Glycyrrhiza Glabra, Salix Nigra, Macrocycstis Pyrifera, Pyrus Malus, Saxifraga Sarmentosa, Vitis Vinfera, Morus Nigra, Scutellaria Baicalensis, Anthemis Nobilis, Salvia Sclarea, Rosmarinus Officianalis, Citrus Medica Limonum, Panax Ginseng, Siegesbeckia Orientalis, Fructus Mume, Ascophyllum Nodosum*, Bifida Ferment lysate, *Glycine Soja* extract, *Beta Vulgaris, Haberlea Rhodopensis, Polygonum Cuspidatun, Citrus Aurantium Dulcis, Vitis Vinifera, Selaginella Tamariscina, Humulus Lupulus, Citrus Reticulata* Peel, *Punica Granatum, Asparagopsis, Curcuma Longa, Menyanthes Trifoliata, Helianthus Annuus, Hordeum Vulgare, Cucumis Sativus, Evernia Prunastri, Evernia Furfuracea*, and mixtures thereof.

B. Oils

In the event the compositions of the invention are in emulsion form, the composition may comprise an oil phase. If present, suggested amounts range from 0.1 to 80%, preferably from 0.5 to 75%, more preferably from 1 to 50%. Suitable oils include silicones, esters, vegetable oils, synthetic oils, including but not limited to those set forth herein. The oils may be volatile or nonvolatile, and are preferably in the form of a pourable liquid at room temperature. The term "volatile" means that the oil has a measurable vapor pressure, or a vapor pressure of at least about 2 mm. of mercury at 20° C. The term "nonvolatile" means that the oil has a vapor pressure of less than about 2 mm. of mercury at 20° C.

1. Volatile Oils

Suitable volatile oils generally have a viscosity ranging from about 0.5 to 5 centistokes 25° C. and include linear silicones, cyclic silicones, paraffinic hydrocarbons, or mixtures thereof. Volatile oils may be used to promote more rapid drying of the skin care composition after it is applied to skin.

(a). Volatile Silicones

Cyclic silicones are one type of volatile silicone that may be used in the composition. Such silicones have the general formula:

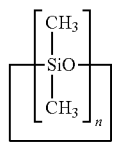

where n=3-6, preferably 4, 5, or 6.

Also suitable are linear volatile silicones, for example, those having the general formula:

where n=0, 1, 2, 3, 4, or 5, preferably 0, 1, 2, 3, or 4.

Cyclic and linear volatile silicones are available from various commercial sources including Dow Corning Corporation and Momentive Performance Materials. The Dow Corning linear volatile silicones are sold under the tradenames Dow Corning 244, 245, 344, and 200 fluids. These fluids include hexamethyldisiloxane (viscosity 0.65 centistokes (abbreviated cst)), octamethyltrisiloxane (1.0 cst), decamethyltetrasiloxane (1.5 cst), dodecamethylpentasiloxane (2 cst) and mixtures thereof, with all viscosity measurements being at 25° C.

Suitable branched volatile silicones include alkyl trimethicones such as methyl trimethicone, a branched volatile silicone having the general formula:

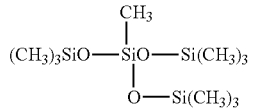

Methyl trimethicone may be purchased from Shin-Etsu Silicones under the tradename TMF-1.5, having a viscosity of 1.5 centistokes at 25° C.

(b). Volatile Paraffinic Hydrocarbons

Also suitable as the volatile oils are various straight or branched chain paraffinic hydrocarbons having 5, 6, 7, 8, 9, 10, 11, 12, 13, 14, 15, 16, 17, 18, 19, or 20 carbon atoms, more preferably 8 to 16 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference.

Preferred volatile paraffinic hydrocarbons have a molecular weight of 70-225, preferably 160 to 190 and a boiling point range of 30 to 320, preferably 60 to 260° C., and a viscosity of less than about 10 cst. at 25° C. Such paraffinic hydrocarbons are available from EXXON under the ISOPARS trademark, and from the Permethyl Corporation and include isododecane and isohexadecane.

2. Non-Volatile Oils

A variety of nonvolatile oils are also suitable for use in the compositions of the invention. The nonvolatile oils generally have a viscosity of greater than about 5 to 10 centistokes at 25° C., and may range in viscosity up to about 1,000,000 centipoise at 25° C. Examples of nonvolatile oils include, but are not limited to:

(a). Esters

Suitable esters are mono-, di-, and triesters. The composition may comprise one or more esters selected from the group, or mixtures thereof.

(i) Monoesters

Monoesters are defined as esters formed by the reaction of a monocarboxylic acid having the formula R—COOH, wherein R is a straight or branched chain saturated or unsaturated alkyl having 2 to 45 carbon atoms, or phenyl; and an alcohol having the formula R—OH wherein R is a straight or branched chain saturated or unsaturated alkyl having 2-30 carbon atoms, or phenyl. Both the alcohol and the acid may be substituted with one or more hydroxyl groups. Either one or both of the acid or alcohol may be a "fatty" acid or alcohol, and may have from about 6 to 30 carbon atoms, more preferably 12, 14, 16, 18, or 22 carbon atoms in straight or branched chain, saturated or unsaturated form. Examples of monoester oils that may be used in the compositions of the invention include hexyl laurate, butyl isostearate, hexadecyl isostearate, cetyl palmitate, isostearyl neopentanoate, stearyl heptanoate, isostearyl isononanoate, steary lactate, stearyl octanoate, stearyl stearate, isononyl isononanoate, and so on.

(ii). Diesters

Suitable diesters are the reaction product of a dicarboxylic acid and an aliphatic or aromatic alcohol or an aliphatic or aromatic alcohol having at least two substituted hydroxyl groups and a monocarboxylic acid. The dicarboxylic acid may contain from 2 to 30 carbon atoms, and may be in the straight or branched chain, saturated or unsaturated form. The dicarboxylic acid may be substituted with one or more hydroxyl groups. The aliphatic or aromatic alcohol may also contain 2 to 30 carbon atoms, and may be in the straight or branched chain, saturated, or unsaturated form. Preferably, one or more of the acid or alcohol is a fatty acid or alcohol, i.e. contains 12-22 carbon atoms. The dicarboxylic acid may also be an alpha hydroxy acid. The ester may be in the dimer or trimer form. Examples of diester oils that may be used in the compositions of the invention include diisostearyl malate, neopentyl glycol dioctanoate, dibutyl sebacate, dicetearyl dimer dilinoleate, dicetyl adipate, diisocetyl adipate, diisononyl adipate, diisostearyl dimer dilinoleate, diisostearyl fumarate, diisostearyl malate, dioctyl malate, and so on.

(iii). Triesters

Suitable triesters comprise the reaction product of a tricarboxylic acid and an aliphatic or aromatic alcohol or alternatively the reaction product of an aliphatic or aromatic alcohol having three or more substituted hydroxyl groups with a monocarboxylic acid. As with the mono- and diesters mentioned above, the acid and alcohol contain 2 to 30 carbon atoms, and may be saturated or unsaturated, straight or branched chain, and may be substituted with one or more hydroxyl groups. Preferably, one or more of the acid or alcohol is a fatty acid or alcohol containing 12 to 22 carbon atoms. Examples of triesters include esters of arachidonic, citric, or behenic acids, such as triarachidin, tributyl citrate, triisostearyl citrate, tri $C_{12-13}$ alkyl citrate, tricaprylin, tricaprylyl citrate, tridecyl behenate, trioctyldodecyl citrate, tridecyl behenate; or tridecyl cocoate, tridecyl isononanoate, and so on.

Esters suitable for use in the composition are further described in the C.T.F.A. Cosmetic Ingredient Dictionary and Handbook, Eleventh Edition, 2006, under the classification of "Esters", the text of which is hereby incorporated by reference in its entirety.

(b). Hydrocarbon Oils

It may be desirable to incorporate one or more nonvolatile hydrocarbon oils into the composition. Suitable nonvolatile hydrocarbon oils include paraffinic hydrocarbons and olefins, preferably those having greater than about 20 carbon atoms. Examples of such hydrocarbon oils include $C_{24-28}$ olefins, $C_{30-45}$ olefins, $C_{20-40}$ isoparaffins, hydrogenated polyisobutene, polyisobutene, polydecene, hydrogenated polydecene, mineral oil, pentahydrosqualene, squalene, squalane, and mixtures thereof. In one preferred embodiment such hydrocarbons have a molecular weight ranging from about 300 to 1000 Daltons.

(c). Glyceryl Esters of Fatty Acids

Synthetic or naturally occurring glyceryl esters of fatty acids, or triglycerides, are also suitable for use in the compositions. Both vegetable and animal sources may be used. Examples of such oils include castor oil, lanolin oil, $C_{10-18}$ triglycerides, caprylic/capric/triglycerides, sweet almond oil, apricot kernel oil, sesame oil, camelina sativa oil, tamanu seed oil, coconut oil, corn oil, cottonseed oil, linseed oil, ink oil, olive oil, palm oil, illipe butter, rapeseed oil, soybean oil, grapeseed oil, sunflower seed oil, walnut oil, and the like.

Also suitable are synthetic or semi-synthetic glyceryl esters, such as fatty acid mono-, di-, and triglycerides which are natural fats or oils that have been modified, for example, mono-, di- or triesters of polyols such as glycerin. In an example, a fatty ($C_{12-22}$) carboxylic acid is reacted with one or more repeating glyceryl groups, glyceryl stearate, diglyceryl diisostearate, polyglyceryl-3 isostearate, polyglyceryl-4 isostearate, polyglyceryl-6 ricinoleate, glyceryl dioleate, glyceryl diisostearate, glyceryl tetraisostearate, glyceryl trioctanoate, diglyceryl distearate, glyceryl linoleate, glyceryl myristate, glyceryl isostearate, PEG castor oils, PEG glyceryl oleates, PEG glyceryl stearates, PEG glyceryl tallowates, and so on.

(d). Nonvolatile Silicones

Nonvolatile silicone oils, both water soluble and water insoluble, are also suitable for use in the composition. Such silicones preferably have a viscosity ranging from about greater than 5 to 800,000 cst, preferably 20 to 200,000 cst at 25° C. Suitable water insoluble silicones include amine functional silicones such as amodimethicone.

For example, such nonvolatile silicones may have the following general formula:

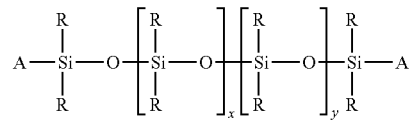

wherein R and R' are each independently $C_{1-30}$ straight or branched chain, saturated or unsaturated alkyl, phenyl or aryl, trialkylsiloxy, and x and y are each independently 1-1,000,000; with the proviso that there is at least one of either x or y, and A is alkyl siloxy endcap unit. Preferred is where A is a methyl siloxy endcap unit; in particular trimethylsiloxy, and R and R' are each independently a $C_{1-30}$ straight or branched chain alkyl, phenyl, or trimethylsiloxy, more preferably a $C_{1-22}$ alkyl, phenyl, or trimethylsiloxy, most preferably methyl, phenyl, or trimethylsiloxy, and resulting silicone is dimethicone, phenyl dimethicone, diphenyl dimethicone, phenyl trimethicone, or trimethylsiloxyphenyl dimethicone. Other examples include alkyl dimethicones such as cetyl dimethicone, and the like wherein at least one R is a fatty alkyl ($C_{12}$, $C_{14}$, $C_{16}$, $C_{18}$, $C_{20}$, or $C_{22}$), and the other R is methyl, and A is a trimethylsiloxy endcap unit, provided such alkyl dimethicone is a pourable liquid at room temperature. Phenyl trimethicone can be purchased from Dow Corning Corporation under the tradename 556 Fluid. Trimethylsiloxyphenyl dimethicone can be purchased from Wacker-Chemie under the tradename PDM-1000. Cetyl dimethicone, also referred to as a liquid silicone wax, may be purchased from Dow Corning as Fluid 2502, or from DeGussa Care & Surface Specialties under the trade names Abii Wax 9801, or 9814.

(e). Fluorinated Oils

Various types of fluorinated oils may also be suitable for use in the compositions including but not limited to fluorinated silicones, fluorinated esters, or perfluoropolyethers. Particularly suitable are fluorosilicones such as trimethylsilyl endcapped fluorosilicone oil, polytrifluoropropylmethylsiloxanes, and similar silicones such as those disclosed in U.S. Pat. No. 5,118,496 which is hereby incorporated by reference. Perfluoropolyethers include those disclosed in U.S. Pat. Nos. 5,183,589, 4,803,067, 5,183,588 all of which are hereby incorporated by reference, which are commercially available from Montefluos under the trademark Fomblin.

C. Aqueous Phase Structuring Agents

In the case where the compositions are in the form of aqueous solutions, dispersions or emulsions, in addition to water the aqueous phase may contain one or more aqueous phase structuring agents, that is, an agent that increases the viscosity or, or thickens, the aqueous phase of the composition. This is particularly desirable when the composition is in the form of a serum or gel. Suitable ranges of aqueous phase structuring agent, if present, are from about 0.01 to 30%, preferably from about 0.1 to 20%, more preferably from about 0.5 to 15% by weight of the total composition. Examples of such agents include various acrylate based thickening agents, natural or synthetic gums, polysaccharides, and the like, including but not limited to those set forth below.

1. Acrylate Polymers

Also suitable are different types of synthetic polymeric thickeners that are other than the polymers set forth above. If present, suggested amounts are from 0.1 to 40%, preferably from about 0.5 to 35%, more preferably from about 1 to 25%.

One type includes acrylic polymeric thickeners comprised of monomers A and B wherein A is selected from the group consisting of acrylic acid, methacrylic acid, and mixtures thereof; and B is selected from the group consisting of a $C_{1-22}$ alkyl acrylate, a $C_{1-22}$ alkyl methacrylate, and mixtures thereof are suitable. In one embodiment the A monomer comprises one or more of acrylic acid or methacrylic acid, and the B monomer is selected from the group consisting of a $C_{1-10}$, most preferably $C_{1-4}$ alkyl acrylate, a $C_{1-10}$, most preferably $C_{1-4}$ alkyl methacrylate, and mixtures thereof. Most preferably the B monomer is one or more of methyl or ethyl acrylate or methacrylate. The acrylic copolymer may be supplied in an aqueous solution having a solids content ranging from about 10-60%, preferably 20-50%, more preferably 25-45% by weight of the polymer, with the remainder water. The composition of the acrylic copolymer may contain from about 0.1-99 parts of the A monomer, and about 0.1-99 parts of the B monomer. Acrylic polymer solutions include those sold by Seppic, Inc., under the tradename Capigel.

Also suitable are acrylic polymeric thickeners that are copolymer of A, B, and C monomers wherein A and B are as defined above, and C has the general formula:

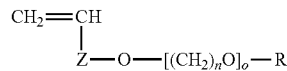

wherein Z is —$(CH_2)_m$; wherein m is 1-10, n is 2-3, o is 2-200, and R is a $C_{10-30}$ straight or branched chain alkyl. Examples of the secondary thickening agent above, are copolymers where A and B are defined as above, and C is CO, and wherein n, o, and R are as above defined. Examples of such secondary thickening agents include acrylates/steareth-20 methacrylate copolymer, which is sold by Rohm & Haas under the tradename Acrysol ICS-1.

Also suitable are acrylate based anionic amphiphilic polymers containing at least one hydrophilic unit and at least one allyl ether unit containing a fatty chain. Preferred are those where the hydrophilic unit contains an ethylenically unsaturated anionic monomer, more specifically a vinyl carboxylic acid such as acrylic acid, methacrylic acid or mixtures thereof, and where the allyl ether unit containing a fatty chain corresponds to the monomer of formula:

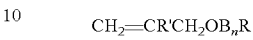

in which R' denotes H or $CH_3$, B denotes the ethyleneoxy radical, n is zero or an integer ranging from 1 to 100, R denotes a hydrocarbon radical selected from alkyl, arylalkyl, aryl, alkylaryl and cycloalkyl radicals which contain from 8 to 30 carbon atoms, preferably from 10 to 24, and even more particularly from 12 to 18 carbon atoms. More preferred in this case is where R' denotes H, n is equal to 10 and R denotes a stearyl (C18) radical. Anionic amphiphilic polymers of this type are described and prepared in U.S. Pat. Nos. 4,677,152 and 4,702,844, both of which are hereby incorporated by reference in their entirety. Among these anionic amphiphilic polymers, polymers formed of 20 to 60% by weight acrylic acid and/or methacrylic acid, of 5 to 60% by weight lower alkyl methacrylates, of 2 to 50% by weight allyl ether containing a fatty chain as mentioned above, and of 0 to 1% by weight of a crosslinking agent which is a well-known copolymerizable polyethylenic unsaturated monomer, for instance diallyl phthalate, allyl (meth)acrylate, divinylbenzene, (poly) ethylene glycol dimethacrylate and methylenebisacrylamide. One commercial example of such polymers are crosslinked terpolymers of methacrylic acid, of ethyl acrylate, of polyethylene glycol (having 10 EO units) ether of stearyl alcohol or steareth-10, in particular those sold by the company Allied Colloids under the names SALCARE SC80 and SALCARE SC90, which are aqueous emulsions containing 30% of a crosslinked terpolymer of methacrylic acid, of ethyl acrylate and of steareth-10 alkyl ether (40/50/10).

Also suitable are acrylate copolymers such as Polyacrylate-3 which is a copolymer of methacrylic acid, methylmethacrylate, methylstyrene isopropylisocyanate, and PEG-40 behenate monomers; Polyacrylate-10 which is a copolymer of sodium acryloyldimethyltaurate, sodium acrylate, acrylamide and vinyl pyrrolidone monomers; or Polyacrylate-11, which is a copolymer of sodium acryloyldimethylacryloyldimethyl taurate, sodium acrylate, hydroxyethyl acrylate, lauryl acrylate, butyl acrylate, and acrylamide monomers.

Also suitable are crosslinked acrylate based polymers where one or more of the acrylic groups may have substituted long chain alkyl (such as 6-40, 10-30, and the like) groups, for example acrylates/$C_{10-30}$ alkyl acrylate crosspolymer which is a copolymer of C10-30 alkyl acrylate and one or more monomers of acrylic acid, methacrylic acid, or one of their simple esters crosslinked with the allyl ether of sucrose or the allyl ether of pentaerythritol. Such polymers are commonly sold under the Carbopol or Pemulen tradenames and have the CTFA name carbomer.

One particularly suitable type of aqueous phase thickening agent are acrylate based polymeric thickeners sold by Clariant under the Aristoflex trademark such as Aristoflex AVC, which is ammonium acryloyldimethyltaurate/VP copolymer; Aristoflex AVL which is the same polymer has found in AVC dispersed in mixture containing caprylic/capric triglyceride, trilaureth-4, and polyglyceryl-2 sesquiisostearate; or Aristoflex HMB which is ammonium acryloyldimethyltaurate/beheneth-25 methacrylate crosspolymer, and the like.

2. High Molecular Weight PEG or Polyglycerins

Also suitable as the aqueous phase thickening agents are various polyethylene glycols (PEG) derivatives where the degree of polymerization ranges from 1,000 to 200,000. Such ingredients are indicated by the designation "PEG" followed by the degree of polymerization in thousands, such as PEG-45M, which means PEG having 45,000 repeating ethylene oxide units. Examples of suitable PEG derivatives include PEG 2M, 5M, 7M, 9M, 14M, 20M, 23M, 25M, 45M, 65M, 90M, 115M, 160M, 180M, and the like.

Also suitable are polyglycerins which are repeating glycerin moieties where the number of repeating moieties ranges from 15 to 200, preferably from about 20-100. Examples of suitable polyglycerins include those having the CFTA names polyglycerin-20, polyglycerin-40, and the like.

D. Oil Phase Structuring Agents

In the case where the composition is anhydrous or in the form of an emulsion, it may be desirable to include one or more oil phase structuring agents in the cosmetic composition. The term "oil phase structuring agent" means an ingredient or combination of ingredients, soluble or dispersible in the oil phase, which will increase the viscosity, or structure, the oil phase. The structuring agent may be present in an amount sufficient to provide a liquid composition with increased viscosity, a semi-solid, or in some cases a solid composition that may be self-supporting. The structuring agent itself may be present in the liquid, semi-solid, or solid form. Suggested ranges of structuring agent are from about 0.01 to 70%, preferably from about 0.05 to 50%, more preferably from about 0.1-35% by weight of the total composition. Suitable oil phase structuring agents include those that are silicone based or organic based. They may be polymers or non-polymers, synthetic, natural, or a combination of both.

1. Silicone Structuring Agents

A variety of oil phase structuring agents may be silicone based, such as silicone gums, silicone waxes, linear silicones having a degree of polymerization that provides the silicone with a degree of viscosity such that when incorporated into the cosmetic composition it is capable of increasing the viscosity of the oil phase. Examples of silicone structuring agents include, but are not limited to:

(a). Silicone Gums

Also suitable for use as an oil phase structuring agent are one or more silicone gums. The term "gum" means a silicone polymer having a degree of polymerization sufficient to provide a silicone having a gum-like texture. In certain cases the silicone polymer forming the gum may be crosslinked. The silicone gum typically has a viscosity ranging from about 500,000 to 100 million cst at 25° C., preferably from about 600,000 to 20 million, more preferably from about 600,000 to 12 million cst. All ranges mentioned herein include all subranges, e.g. 550,000; 925,000; 3.5 million.

The silicone gums that are used in the compositions include, but are not limited to, those of the general formula wherein:

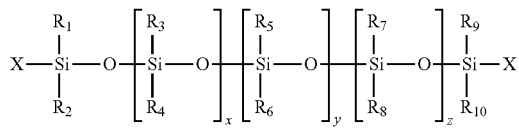

$R_1$ to $R_9$ are each independently an alkyl having 1 to 30 carbon atoms, aryl, or aralkyl; and X is OH or a $C_{1-30}$ alkyl, or vinyl; and wherein x, y, or z may be zero with the proviso that no more than two of x, y, or z are zero at any one time, and further that x, y, and z are such that the silicone gum has a viscosity of at least about 500,000 cst, ranging up to about 100 million centistokes at 25° C. Preferred is where R is methyl or OH.

Such silicone gums may be purchased in pure form from a variety of silicone manufacturers including Wacker-Chemie or Dow Corning, and the like. Such silicone gums include those sold by Wacker-Belsil under the trade names CM3092, Wacker-Belsil 1000, or Wacker-Belsil DM 3096. A silicone gum where X is OH, also referred to as dimethiconol, is available from Dow Corning Corporation under the trade name 1401. The silicone gum may also be purchased in the form of a solution or dispersion in a silicone compatible vehicle such as volatile or nonvolatile silicone. An example of such a mixture may be purchased from Barnet Silicones under the HL-88 tradename, having the INCI name dimethicone.

(b). Silicone Waxes

Another type of oily phase structuring agent includes silicone waxes that are typically referred to as alkyl silicone waxes which are semi-solids or solids at room temperature. The term "alkyl silicone wax" means a polydimethylsiloxane having a substituted long chain alkyl (such as C16 to 30) that confers a semi-solid or solid property to the siloxane. Examples of such silicone waxes include stearyl dimethicone, which may be purchased from DeGussa Care & Surface Specialties under the tradename Abil Wax 9800 or from Dow Corning under the tradename 2503. Another example is bis-stearyl dimethicone, which may be purchased from Gransil Industries under the tradename Gransil A-18, or behenyl dimethicone, behenoxy dimethicone.

(c). Polyamides or Silicone Polyamides

Also suitable as oil phase structuring agents are various types of polymeric compounds such as polyamides or silicone polyamides.

The term silicone polyamide means a polymer comprised of silicone monomers and monomers containing amide groups as further described herein. The silicone polyamide preferably comprises moieties of the general formula:

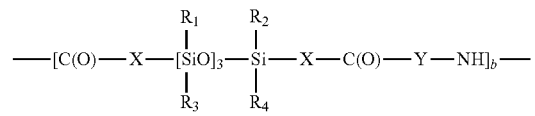

X is a linear or branched alkylene having from about 1-30 carbon atoms; $R_1$, $R_2$, $R_3$, and $R_4$ are each independently $C_{1-30}$ straight or branched chain alkyl which may be substituted with one or more hydroxyl or halogen groups; phenyl which may be substituted with one or more $C_{1-30}$ alkyl groups, halogen, hydroxyl, or alkoxy groups; or a siloxane chain having the general formula:

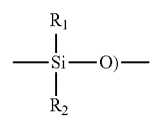

and Y is:
(a) a linear or branched alkylene having from about 1-40 carbon atoms which may be substituted with:
(i) one or more amide groups having the general formula $R_1CONR_1$, or (ii) $C_{5-6}$ cyclic ring, or
(iii) phenylene which may be substituted with one or more $C_{1-10}$ alkyl groups, or
(iv) hydroxy, or
(v) $C_{3-8}$ cycloalkane, or
(vi) $C_{1-20}$ alkyl which may be substituted with one or more hydroxy groups, or
(vii) $C_{1-10}$ alkyl amines; or (b) $TR_5R_6R_7$ wherein $R_5$, $R_6$, and $R_7$, are each independently a $C_{1-10}$ linear or branched alkylenes, and T is $CR_8$ wherein $R_8$ is hydrogen, a trivalent atom N, P, or Al, or a $C_{1-30}$ straight or branched chain alkyl which may be substituted with one or more hydroxyl or halogen groups; phenyl which may be substituted with one or more $C_{1-30}$ alkyl groups, halogen, hydroxyl, or alkoxy groups; or a siloxane chain having the general formula:

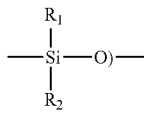

Preferred is where $R_1$, $R_2$, $R_3$, and $R_4$ are $C_{1-10}$, preferably methyl; and X and Y is a linear or branched alkylene. Preferred are silicone polyamides having the general formula:

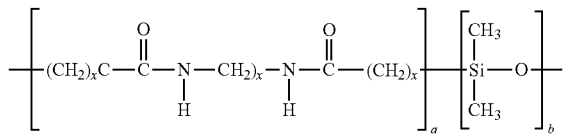

wherein a and b are each independently sufficient to provide a silicone polyamide polymer having a melting point ranging from about 60 to 120° C., and a molecular weight ranging from about 40,000 to 500,000 Daltons. One type of silicone polyamide that may be used in the compositions of the invention may be purchased from Dow Corning Corporation under the tradename Dow Corning 2-8178 gellant which has the CTFA name nylon-611/dimethicone copolymer which is sold in a composition containing PPG-3 myristyl ether.

Also suitable are polyamides such as those purchased from Arizona Chemical under the tradenames Uniclear and Sylvaclear. Such polyamides may be ester terminated or amide terminated. Examples of ester terminated polyamides include, but are not limited to those having the general formula:

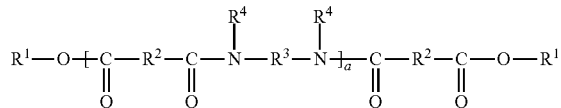

wherein n denotes a number of amide units such that the number of ester groups ranges from about 10% to 50% of the total number of ester and amide groups; each $R_1$ is independently an alkyl or alkenyl group containing at least 4 carbon atoms; each $R_2$ is independently a $C_{4-42}$ hydrocarbon group, with the proviso that at least 50% of the $R_2$ groups are a C30-42 hydrocarbon; each $R_3$ is independently an organic group containing at least 2 carbon atoms, hydrogen atoms and optionally one or more oxygen or nitrogen atoms; and each $R_4$ is independently a hydrogen atom, a $C_{1-10}$ alkyl group or a direct bond to $R_3$ or to another $R_4$, such that the nitrogen atom to which $R_3$ and $R_4$ are both attached forms part of a heterocyclic structure defined by $R_4$—N—$R_3$, with at least 50% of the groups $R_4$ representing a hydrogen atom.

General examples of ester and amide terminated polyamides that may be used as oil phase gelling agents include those sold by Arizona Chemical under the tradenames Sylvaclear A200V or A2614V, both having the CTFA name ethylenediamine/hydrogenated dimer dilinoleate copolymer/bis-di-$C_{14-18}$ alkyl amide; Sylvaclear AF1900V; Sylvaclear C75V having the CTFA name bis-stearyl ethylenediamine/neopentyl glycol/stearyl hydrogenated dimer dilinoleate copolymer; Sylvaclear PA1200V having the CTFA name Polyamide-3; Sylvaclear PE400V; Sylvaclear WF1500V; or Uniclear, such as Uniclear 100VG having the INCI name ethylenediamine/stearyl dimer dilinoleate copolymer; or ethylenediamine/stearyl dimer ditallate copolymer. Other examples of suitable polyamides include those sold by Henkel under the Versamid trademark (such as Versamid 930, 744, 1655), or by Olin Mathieson Chemical Corp. under the brand name Onamid S or Onamid C.

(d). Natural or Synthetic Organic Waxes

Also suitable as the oil phase structuring agent may be one or more natural or synthetic waxes such as animal, vegetable, or mineral waxes. Preferably such waxes will have a higher melting point such as from about 50 to 150° C., more preferably from about 65 to 100° C. Examples of such waxes include waxes made by Fischer-Tropsch synthesis, such as polyethylene or synthetic wax; or various vegetable waxes such as bayberry, candelilla, ozokerite, *acacia*, beeswax, ceresin, cetyl esters, flower wax, *citrus* wax, carnauba wax, jojoba wax, japan wax, polyethylene, microcrystalline, rice bran, lanolin wax, mink, montan, bayberry, ouricury, ozokerite, palm kernel wax, paraffin, avocado wax, apple wax, shellac wax, clary wax, spent grain wax, grape wax, and polyalkylene glycol derivatives thereof such as PEG 6-20 beeswax, or PEG-12 carnauba wax; or fatty acids or fatty alcohols, including esters thereof, such as hydroxystearic acids (for example 12-hydroxy stearic acid), tristearin, tribehenin, and so on.

(e). Montmorillonite Minerals

One type of structuring agent that may be used in the composition comprises natural or synthetic montmorillonite minerals such as hectorite, bentonite, and quaternized derivatives thereof, which are obtained by reacting the minerals with a quaternary ammonium compound, such as stearalkonium bentonite, hectorites, quaternized hectorites such as Quaternium-18 hectorite, attapulgite, carbonates such as propylene carbonate, bentones, and the like.

(f). Silicas and Silicates

Another type of structuring agent that may be used in the compositions are silicas, silicates, silica silylate, and alkali metal or alkaline earth metal derivatives thereof. These silicas and silicates are generally found in the particulate form and include silica, silica silylate, magnesium aluminum silicate, and the like.

E. Surfactants

The composition may contain one or more surfactants, especially if in the emulsion form. However, such surfactants may be used if the compositions are anhydrous also, and will assist in dispersing ingredients that have polarity, for example pigments. Such surfactants may be silicone or organic based. The surfactants will aid in the formation of stable emulsions of either the water-in-oil or oil-in-water form. If present, the surfactant may range from about 0.001 to 30%, preferably from about 0.005 to 25%, more preferably from about 0.1 to 20% by weight of the total composition.

1. Silicone Surfactants

Suitable silicone surfactants include polyorganosiloxane polymers that have amphiphilic properties, for example contain hydrophilic radicals and lipophilic radicals. These silicone surfactants may be liquids or solids at room temperature.

(a). Dimethicone Copolyols or Alkyl Dimethicone Copolyols

One type of silicone surfactant that may be used is generally referred to as dimethicone copolyol or alkyl dimethicone copolyol. This surfactant is either a water-in-oil or oil-in-water surfactant having an Hydrophile/Lipophile Balance (HLB) ranging from about 2 to 18. Preferably the silicone surfactant is a nonionic surfactant having an HLB ranging from about 2 to 12, preferably about 2 to 10, most preferably about 4 to 6. The term "hydrophilic radical" means a radical that, when substituted onto the organosiloxane polymer backbone, confers hydrophilic properties to the substituted portion of the polymer. Examples of radicals that will confer hydrophilicity are hydroxy-polyethyleneoxy, hydroxyl, carboxylates, and mixtures thereof. The term "lipophilic radical" means an organic radical that, when substituted onto the organosiloxane polymer backbone, confers lipophilic properties to the substituted portion of the polymer. Examples of organic radicals that will confer lipophilicity are $C_{1-40}$ straight or branched chain alkyl, fluoro, aryl, aryloxy, $C_{1-40}$ hydrocarbyl acyl, hydroxy-polypropyleneoxy, or mixtures thereof.

One type of suitable silicone surfactant has the general formula:

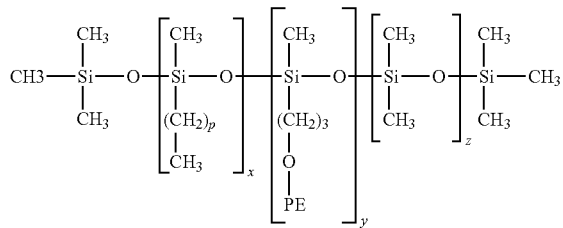

wherein p is 0-40 (the range including all numbers between and subranges such as 2, 3, 4, 13, 14, 15, 16, 17, 18, etc.), and PE is $(-C_2H_4O)_a-(-C_3H_6O)_b-H$ wherein a is 0 to 25, b is 0-25 with the proviso that both a and b cannot be 0 simultaneously, x and y are each independently ranging from 0 to 1 million with the proviso that they both cannot be 0 simultaneously. In one preferred embodiment, x, y, z, a, and b are such that the molecular weight of the polymer ranges from about 5,000 to about 500,000, more preferably from about 10,000 to 100,000, and is most preferably approximately about 50,000 and the polymer is generically referred to as dimethicone copolyol.

One type of silicone surfactant is wherein p is such that the long chain alkyl is cetyl or lauryl, and the surfactant is called, generically, cetyl dimethicone copolyol or lauryl dimethicone copolyol respectively.

In some cases the number of repeating ethylene oxide or propylene oxide units in the polymer are also specified, such as a dimethicone copolyol that is also referred to as PEG-15/PPG-10 dimethicone, which refers to a dimethicone having substituents containing 15 ethylene glycol units and 10 propylene glycol units on the siloxane backbone. It is also possible for one or more of the methyl groups in the above general structure to be substituted with a longer chain alkyl (e.g. ethyl, propyl, butyl, etc.) or an ether such as methyl ether, ethyl ether, propyl ether, butyl ether, and the like.

Examples of silicone surfactants are those sold by Dow Corning under the tradename Dow Corning 3225C Formulation Aid having the CTFA name cyclotetrasiloxane (and) cyclopentasiloxane (and) PEG/PPG-18 dimethicone; or 5225C Formulation Aid, having the CTFA name cyclopentasiloxane (and) PEG/PPG-18/18 dimethicone; or Dow Corning 190 Surfactant having the CTFA name PEG/PPG-18/18 dimethicone; or Dow Corning 193 Fluid, Dow Corning 5200 having the CTFA name lauryl PEG/PPG-18/18 methicone; or Abil EM 90 having the CTFA name cetyl PEG/PPG-14/14 dimethicone sold by Goldschmidt; or Abil EM 97 having the CTFA name bis-cetyl PEG/PPG-14/14 dimethicone sold by Goldschmidt; or Abil WE 09 having the CTFA name cetyl PEG/PPG-10/1 dimethicone in a mixture also containing polyglyceryl-4 isostearate and hexyl laurate; or KF-6011 sold by Shin-Etsu Silicones having the CTFA name PEG-11 methyl ether dimethicone; KF-6012 sold by Shin-Etsu Silicones having the CTFA name PEG/PPG-20122 butyl ether dimethicone; or KF-6013 sold by Shin-Etsu Silicones having the CTFA name PEG-9 dimethicone; or KF-6015 sold by Shin-Etsu Silicones having the CTFA name PEG-3 dimethicone; or KF-6016 sold by Shin-Etsu Silicones having the CTFA name PEG-9 methyl ether dimethicone; or KF-6017 sold by Shin-Etsu Silicones having the CTFA name PEG-10 dimethicone; or KF-6038 sold by Shin-Etsu Silicones having the CTFA name lauryl PEG-9 polydimethylsiloxyethyl dimethicone.

(b). Crosslinked Silicone Surfactants

Also suitable are various types of crosslinked silicone surfactants that are often referred to as emulsifying elastomers. They are typically prepared as set forth above with respect to the section "silicone elastomers" except that the silicone elastomers will contain at least one hydrophilic moiety such as polyoxyalkylenated groups. Typically these polyoxyalkylenated silicone elastomers are crosslinked organopolysiloxanes that may be obtained by a crosslinking addition reaction of diorganopolysiloxane comprising at least one hydrogen bonded to silicon and of a polyoxyalkylene comprising at least two ethylenically unsaturated groups. In at least one embodiment, the polyoxyalkylenated crosslinked organopolysiloxanes are obtained by a crosslinking addition reaction of a diorganopolysiloxane comprising at least two hydrogens each bonded to a silicon, and a polyoxyalkylene comprising at least two ethylenically unsaturated groups, optionally in the presence of a platinum catalyst, as described, for example, in U.S. Pat. No. 5,236,986 and U.S. Pat. No. 5,412,004, U.S. Pat. No. 5,837,793 and U.S. Pat. No. 5,811,487, the contents of which are incorporated by reference.

Polyoxyalkylenated silicone elastomers that may be used in at least one embodiment of the invention include those sold by Shin-Etsu Silicones under the names KSG-21, KSG-20, KSG-30, KSG-31, KSG-32, KSG-33; KSG-210 which is dimethicone/PEG-10/15 crosspolymer dispersed in dimethicone; KSG-310 which is PEG-IS lauryl dimethicone crosspolymer; KSG-320 which is PEG-5S lauryl dimethicone crosspolymer dispersed in isododecane; KSG-330 (the former dispersed in triethylhexanoin), KSG-340 which is a mixture of PEG-10 lauryl dimethicone crosspolymer and PEG-15 lauryl dimethicone crosspolymer.

Also suitable are polyglycerolated silicone elastomers like those disclosed in PCT/WO 2004/024798, which is hereby incorporated by reference in its entirety. Such elastomers include Shin-Etsu's KSG series, such as KSG-710 which is dimethicone/polyglycerin-3 crosspolymer dispersed in dimethicone; or lauryl dimethicone/polyglycerin-3 crosspolymer dispersed in a variety of solvent such as isododecane, dimethicone, triethylhexanoin, sold under the Shin-Etsu tradenames KSG-810, KSG-820, KSG-830, or KSG-840. Also suitable are silicones sold by Dow Corning under the tradenames 9010 and DC9011.

One preferred crosslinked silicone elastomer emulsifier is dimethicone/PEG-10/15 crosspolymer, which provides excellent aesthetics due to its elastomeric backbone, but also surfactancy properties.

(c). Organic Nonionic Surfactants

The composition may comprise one or more nonionic organic surfactants. Suitable nonionic surfactants include alkoxylated alcohols, or ethers, formed by the reaction of an alcohol with an alkylene oxide, usually ethylene or propylene oxide. Preferably the alcohol is either a fatty alcohol having 6 to 30 carbon atoms. Examples of such ingredients include Steareth 2-100, which is formed by the reaction of stearyl alcohol and ethylene oxide and the number of ethylene oxide units ranges from 2 to 100; Beheneth 5-30 which is formed by the reaction of behenyl alcohol and ethylene oxide where the number of repeating ethylene oxide units is 5 to 30; Ceteareth 2-100, formed by the reaction of a mixture of cetyl and stearyl alcohol with ethylene oxide, where the number of repeating ethylene oxide units in the molecule is 2 to 100; Ceteth 1-45 which is formed by the reaction of cetyl alcohol and ethylene oxide, and the number of repeating ethylene oxide units is 1 to 45, and so on.

Other alkoxylated alcohols are formed by the reaction of fatty acids and mono-, di- or polyhydric alcohols with an alkylene oxide. For example, the reaction products of $C_{6-30}$ fatty carboxylic acids and polyhydric alcohols which are monosaccharides such as glucose, galactose, methyl glucose, and the like, with an alkoxylated alcohol. Examples include polymeric alkylene glycols reacted with glyceryl fatty acid esters such as PEG glyceryl oleates, PEG glyceryl stearate; or PEG polyhydroxyalkanotes such as PEG dipolyhydroxystearate wherein the number of repeating ethylene glycol units ranges from 3 to 1000.

Also suitable as nonionic surfactants are formed by the reaction of a carboxylic acid with an alkylene oxide or with a polymeric ether. The resulting products have the general formula:

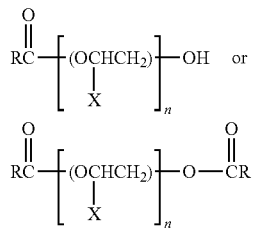

where RCO is the carboxylic ester radical, X is hydrogen or lower alkyl, and n is the number of polymerized alkoxy groups. In the case of the diesters, the two RCO-groups do not need to be identical. Preferably, R is a C6-30 straight or branched chain, saturated or unsaturated alkyl, and n is from 1-100.

Monomeric, homopolymeric, or block copolymeric ethers are also suitable as nonionic surfactants. Typically, such ethers are formed by the polymerization of monomeric alkylene oxides, generally ethylene or propylene oxide. Such polymeric ethers have the following general formula:

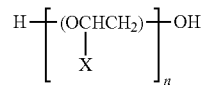

wherein R is H or lower alkyl and n is the number of repeating monomer units, and ranges from 1 to 500.

Other suitable nonionic surfactants include alkoxylated sorbitan and alkoxylated sorbitan derivatives. For example, alkoxylation, in particular ethoxylation of sorbitan provides polyalkoxylated sorbitan derivatives. Esterification of polyalkoxylated sorbitan provides sorbitan esters such as the polysorbates. For example, the polyalkoxylated sorbitan can be esterified with C6-30, preferably C12-22 fatty acids. Examples of such ingredients include Polysorbates 20-85, sorbitan oleate, sorbitan sesquioleate, sorbitan palmitate, sorbitan sesquiisostearate, sorbitan stearate, and so on.

Certain types of amphoteric, zwitterionic, or cationic surfactants may also be used in the compositions. Descriptions of such surfactants are set forth in U.S. Pat. No. 5,843,193, which is hereby incorporated by reference in its entirety.

F. Sunscreens

It may also be desirable to include one or more sunscreens in the compositions of the invention. Such sunscreens include chemical UVA or UVB sunscreens or physical sunscreens in the particulate form.

1. UVA Chemical Sunscreens

If desired, the composition may comprise one or more UVA sunscreens. The term "UVA sunscreen" means a chemical compound that blocks UV radiation in the wavelength range of about 320 to 400 nm. Preferred UVA sunscreens are dibenzoylmethane compounds having the general formula:

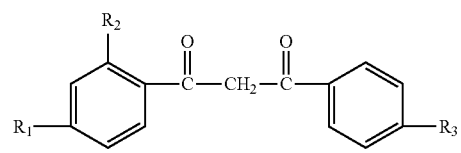

wherein $R_1$ is H, OR and NRR wherein each R is independently H, $C_{1-20}$ straight or branched chain alkyl; $R_2$ is H or OH; and $R_3$ is H, $C_{1-20}$ straight or branched chain alkyl.

Preferred is where $R_1$ is OR where R is a $C_{1-20}$ straight or branched alkyl, preferably methyl; $R_2$ is H; and $R_3$ is a $C_{1-20}$ straight or branched chain alkyl, more preferably, butyl.

Examples of suitable UVA sunscreen compounds of this general formula include 4-methyldibenzoylmethane, 2-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'diisopropylbenzoylmethane, 4-tert-butyl-4'-methoxydibenzoylmethane, 4,4'-diisopropylbenzoylmethane, 2-methyl-5-isopropyl-4'-methoxydibenzoylmethane, 2-methyl-5-tert-butyl-4'-methoxydibenzoylmethane, and so on. Particularly preferred is 4-tert-butyl-4'-methoxydibenzoylmethane, also referred to as Avobenzone. Avobenzone is commercial available from Givaudan-Roure under the trademark Parsol 1789, and Merck & Co. under the tradename Eusolex 9020.

Other types of UVA sunscreens include dicamphor sulfonic acid derivatives, such as ecamsule, a sunscreen sold under the trade name Mexoryl™, which is terephthalylidene dicamphor sulfonic acid, having the formula:

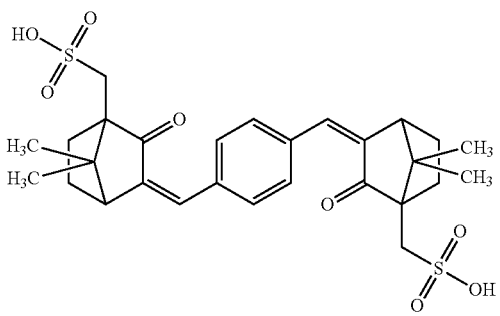 [SMILES: CC1(C)C2CCC1(CS(=O)(=O)O)C(=O)/C2=C\c1ccc(/C=C2\C(=O)C3(CS(=O)(=O)O)CCC2C3(C)C)cc1]

The composition may contain from about 0.001-20%, preferably 0.005-5%, more preferably about 0.005-3% by weight of the composition of UVA sunscreen. In the preferred embodiment of the invention the UVA sunscreen is Avobenzone, and it is present at not greater than about 3% by weight of the total composition.

2. UVB Chemical Sunscreens

The term "UVB sunscreen" means a compound that blocks UV radiation in the wavelength range of from about 290 to 320 nm. A variety of UVB chemical sunscreens exist including alpha-cyano-beta,beta-diphenyl acrylic acid esters as set forth in U.S. Pat. No. 3,215,724, which is hereby incorporated by reference in its entirety. One particular example of an alpha-cyano-beta,beta-diphenyl acrylic acid ester is Octocrylene, which is 2-ethylhexyl 2-cyano-3,3-diphenylacrylate. In certain cases the composition may contain no more than about 110% by weight of the total composition of octocrylene. Suitable amounts range from about 0.001-10% by weight. Octocrylene may be purchased from BASF under the tradename Uvinul N-539.

Other suitable sunscreens include benzylidene camphor derivatives as set forth in U.S. Pat. No. 3,781,417, which is hereby incorporated by reference in its entirety. Such benzylidene camphor derivatives have the general formula:

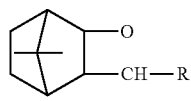

wherein R is p-tolyl or styryl, preferably styryl. Particularly preferred is 4-methylbenzylidene camphor, which is a lipid soluble UVB sunscreen compound sold under the tradename Eusolex 6300 by Merck.

Also suitable are cinnamate derivatives having the general formula:

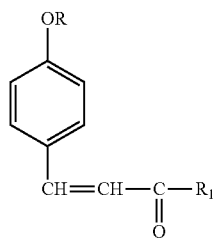

wherein R and $R_1$ are each independently a $C_{1-20}$ straight or branched chain alkyl. Preferred is where R is methyl and $R_1$ is a branched chain $C_{1-10}$, preferably $C_8$ alkyl. The preferred compound is ethylhexyl methoxycinnamate, also referred to as Octoxinate or octyl methoxycinnamate. The compound may be purchased from Givaudan Corporation under the tradename Parsol MCX, or BASF under the tradename Uvinul MC 80. Also suitable are mono-, di-, and triethanolamine derivatives of such methoxy cinnamates including diethanolamine methoxycinnamate. Cinoxate, the aromatic ether derivative of the above compound is also acceptable. If present, the Cinoxate should be found at no more than about 3% by weight of the total composition.

Also suitable as UVB screening agents are various benzophenone derivatives having the general formula:

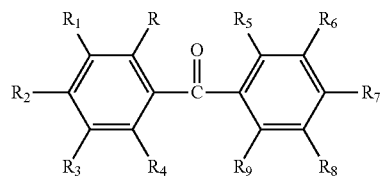

wherein R through $R_9$ are each independently H, OH, $NaO_3S$, $SO_3H$, $SO_3Na$, Cl, R", OR" where R" is $C_{1-20}$ straight or branched chain alkyl Examples of such compounds include Benzophenone 1, 2, 3, 4, 5, 6, 7, 8, 9, 10, 11, and 12. Particularly preferred is where the benzophenone derivative is Benzophenone 3 (also referred to as Oxybenzone), Benzophenone 4 (also referred to as Sulisobenzone), Benzophenone 5 (Sulisobenzone Sodium), and the like. Most preferred is Benzophenone 3.

Also suitable are certain menthyl salicylate derivatives having the general formula:

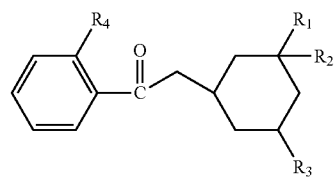

wherein $R_1$, $R_2$, $R_3$, and $R_4$ are each independently H, OH, $NH_2$, or $C_{1-20}$ straight or branched chain alkyl. Particularly preferred is where $R_1$, $R_2$, and $R_3$ are methyl and $R_4$ is hydroxyl or $NH_2$, the compound having the name homomethyl salicylate (also known as Homosalate) or menthyl anthranilate. Homosalate is available commercially from Merck under the tradename Eusolex HMS and menthyl anthranilate is commercially available from Haarmann & Reimer under the tradename Heliopan. If present, the Homosalate should be found at no more than about 15% by weight of the total composition.

Various amino benzoic acid derivatives are suitable UVB absorbers including those having the general formula:

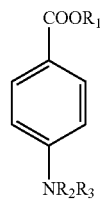

wherein $R_1$, $R_2$, and $R_3$ are each independently H, $C_{1-20}$ straight or branched chain alkyl which may be substituted with one or more hydroxy groups. Particularly preferred is wherein $R_1$ is H or $C_{1-8}$ straight or branched alkyl, and $R_2$ and $R_3$ are H, or $C_{1-8}$ straight or branched chain alkyl. Particularly preferred are PABA, ethyl hexyl dimethyl PABA (Padimate O), ethyldihydroxypropyl PABA, and the like. If present Padimate O should be found at no more than about 8% by weight of the total composition.

Salicylate derivatives are also acceptable UVB absorbers. Such compounds have the general formula:

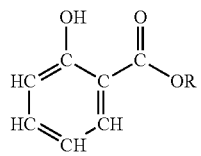

wherein R is a straight or branched chain alkyl, including derivatives of the above compound formed from mono-, di-, or triethanolamines. Particular preferred are octyl salicylate, TEA-salicylate, DEA-salicylate, and mixtures thereof.

Generally, the amount of the UVB chemical sunscreen present may range from about 0.001-45%, preferably 0.005-40%, more preferably about 0.01-35% by weight of the total composition.

Also suitable are particulate sunscreens such as zinc oxide or titanium dioxide, which may have particle sizes ranging from 0.1 to 100 microns.

If desired, the compositions of the invention may be formulated to have a certain SPF (sun protective factor) values ranging from about 1-50, preferably about 2-45, most preferably about 5-30. Calculation of SPF values is well known in the art.

G. Particulate Materials

The compositions of the invention may contain particulate materials in the form of pigments, inert particulates, or mixtures thereof. If present, suggested ranges are from about 0.01-75%, preferably about 0.5-70%, more preferably about 0.1-65% by weight of the total composition. In the case where the composition may comprise mixtures of pigments and powders, suitable ranges include about 0.01-75% pigment and 0.1-75% powder, such weights by weight of the total composition.

1. Powders

The particulate matter may be colored or non-colored (for example white) non-pigmented powders. Suitable non-pigmented powders include bismuth oxychloride, titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above mentioned powders may be surface treated with lecithin, amino acids, mineral oil, silicone, or various other agents either alone or in combination, which coat the powder surface and render the particles more lipophilic in nature.

2. Pigments

The particulate materials may comprise various organic and/or inorganic pigments. The organic pigments are generally various aromatic types including azo, indigoid, triphenylmethane, anthroquinone, and xanthine dyes which are designated as D&C and FD&C blues, browns, greens, oranges, reds, yellows, etc. Organic pigments generally consist of insoluble metallic salts of certified color additives, referred to as the Lakes. Inorganic pigments include iron oxides, ultramarines, chromium, chromium hydroxide colors, and mixtures thereof. Iron oxides of red, blue, yellow, brown, black, and mixtures thereof are suitable.

H. Preservatives

The composition may contain 0.001-8%, preferably 0.01-6%, more preferably 0.05-5% by weight of the total composition of preservatives. A variety of preservatives are suitable, including such as benzoic acid, benzyl alcohol, benzylhemiformal, benzylparaben, 5-bromo-5-nitro-1,3-dioxane, 2-bromo-2-nitropropane-1,3-diol, butyl paraben, phenoxyethanol, methyl paraben, propyl paraben, diazolidinyl urea, calcium benzoate, calcium propionate, caprylyl glycol, biguanide derivatives, phenoxyethanol, captan, chlorhexidine diacetate, chlorhexidine digluconate, chlorhexidine dihydrochloride, chloroacetamide, chlorobutanol, p-chloro-m-cresol, chlorophene, chlorothymol, chloroxylenol, m-cresol, o-cresol, DEDM Hydantoin, DEDM Hydantoin dilaurate, dehydroacetic acid, diazolidinyl urea, dibromopropamidine diisethionate, DMDM Hlydantoin, and the like. In one preferred embodiment the composition is free of parabens.

1. Vitamins and Antioxidants

The compositions of the invention may contain vitamins and/or coenzymes, as well as antioxidants. If so, 0.001-10%, preferably 0.01-8%, more preferably 0.05-5% by weight of the total composition is suggested. Suitable vitamins include ascorbic acid and derivatives thereof such as ascorbyl palmitate, tetrahexydecyl ascorbate, and so on, the B vitamins such as thiamine, riboflavin, pyridoxin, and so on, as well as coenzymes such as thiamine pyrophosphate, flavin adenin dinucleotide, folic acid, pyridoxal phosphate, tetrahydrofolic acid, and so on. Also Vitamin A and derivatives thereof are suitable. Examples are retinyl palmitate, retinol, retinoic acid, as well as Vitamin A in the form of beta carotene. Also suitable is Vitamin E and derivatives thereof such as Vitamin E acetate, nicotinate, or other esters thereof. In addition, Vitamins D and K are suitable.

Suitable antioxidants are ingredients which assist in preventing or retarding spoilage. Examples of antioxidants suitable for use in the compositions of the invention are potassium sulfite, sodium bisulfite, sodium erythorbate, sodium metabisulfite, sodium sulfite, propyl gallate, cysteine hydrochloride, butylated hydroxytoluene, butylated hydroxyanisole, and so on.

VI. The Form of the Compositions

The compositions may be in the form of anhydrous compositions, solutions, or emulsions in water-in-oil or oil-in-water form. The compositions may be liquid, solid, or semi-solid. If in the form of emulsions, from about 0.1 to 80% water and from about 0.1 to 80% water may be present. If in the anhydrous form the compositions typically contain oil and other ingredients such as powders, pigments, oils, or structuring agents. If in the solution form the compositions contain from about 0.1 to 80% water and other water soluble or dispersible ingredients.

The compositions may be in the form of those applied to skin such as creams, lotions, serums, gels, etc., or color cosmetics such as foundations, concealers, eye shadow, eye liner, mascara, blush, lipstick, lip gloss, and the like.

The compositions may also be in the form of hair care products such as shampoos, conditioners, styling products and the like. Also suitable forms include nail care products such as gels, cuticle creams, and the like.

In one preferred embodiment of the invention the composition is a skin cream comprising:
- 10-85% water,
- 0.5-10% Polymer,
- 1-25% moisturizer selected from the group consisting of urea, hydroxyethyl urea, glycerin, shea butter, myristyl myristate, pentaerythrityl distearate, acetylated glycol stearate, sodium stearoyl glutamate, hydrogenated polyisobutene, hydrogenated lecithin, pentylene glycol, glucose, dimethicone, sodium hyaluronate, VP/VA copolymer, Ceramide III, amodimethicone, and mixtures thereof;
- 0.5-20% of a silicone elastomer, preferably dimethicone/vinyl dimethicone crosspolymer or vinyl dimethicone/methicone/silsesquioxane copolymer; and
- 0.1-5% of a botanical extract, preferably *Alicaligenes polysaccharide*, *Laminaria digitata* extract, *Hypnea musciformis* extract, algae extract, and mixtures thereof.

In another preferred embodiment the composition is a primer composition in oil in water emulsion form for application to skin or under eye area to reduce appearance of defects such as dark under eye circles comprising:
- 10-80% water,
- 1-35% Polymer,
- 1-20% glycerin,
- 1-20% of a fluorinated hydrocarbon preferably selected from the group consisting of perfluorodecalin, methyl perfluorobutyl ether, perfluorohexane and mixtures thereof;
- 1-20% silicone elastomer, preferably selected from the group consisting dimethicone/vinyl dimethicone crosspolymer or vinyl dimethicone/methylsilsesquioxane copolymer,
- 0.1-10% botanical extract,
- 0.5-20% nonionic surfactant; and
- 1-35% particulates comprising pigments and powders.

In another preferred embodiment the composition is a primer that changes color upon application to skin from a first resting color to a second application color, comprising:
- 10-85% water,
- 1-20% glycerin,
- 0.5-20% Polymer,
- 2-25% low viscosity evaporable liquid, preferably a volatile silicone, hydrocarbon, or perfluorinated ingredient,
- 0.01-20% of water soluble pigment, preferably galactoarabinan coated pigments, and
- Optionally 0.01-5% of a ceramide; and
- Optionally from 0.5 to 15% of a silicone elastomer.

In another preferred embodiment the composition is an aqueous based solid stick that optionally cools the skin upon application, comprising:
- 1-25% glycerin,
- 1-15% silicone elastomer,
- 0.5 to 20% Polymer,
- 0.1 to 5% sugar alcohol such as sorbitol,
- 0.5 to 10% of a humectants such as butylene or propylene glycol.

In another preferred embodiment the composition is a serum comprising:
- 5-90% water,
- 3-25% glycerin,
- 0.5-20% Polymer,
- 0.5-20% silicone, preferably dimethicone,
- 0.1-15% humectants, preferably butylene glycol,
- 0.1-10% sodium hyaluronate,
- 0.1-5% sugar alcohol such as sorbitol,
- 0.1-5% sugar, and
- 0.001-5% ceramide.

In another preferred embodiment the composition is a cream or lotion in oil in water emulsion form comprising:
- 1-85% water,
- 0.1-25% Polymer,
- 0.1-20% silicone elastomer,
- 0.1-10% humectant such as butylene glycol or trehalose,
- Optionally 0.1-10% Polyquaternium-41,
- Optionally 0.1-10% sugar (such as glucose, fructose, etc.)
- Optionally 0.01-10% botanical extract.

In addition to the above, the compositions of the invention can exist in a variety of other forms, such as emulsions, suspensions, dispersions, solutions, and anhydrous compositions.

VII. The Methods of the Composition

A. Method for Moisturizing and/or Blurring the Appearance of Skin Defects

The composition of the invention may be used in a method for moisturizing a keratin surface and/or blurring the appearance of defects thereon, preferably by de-glossing, by topically applying to a surface in need of moisturization or having defects that need to be blurred, a composition containing the Polymer. In the method the composition containing the Polymer may be applied to the desired keratin surface one or more times per day and in the form of a cream, lotion, gel, or anhydrous product. Preferably the composition is aqueous based and the keratin surface is skin. When the composition is applied it will moisturize skin and provide excellent blurring of skin defects such as depressions, uneven pigmentation, blemishes, scars, and the like. Example 3 demonstrates that the invention composition and Polymer provides superior moisturization when compared with commercially available gold standard moisturizers. Examples 4, 5, and 6 demonstrate that Polymer has optimal activity in blurring the appearance of skin defects, for example, by de-glossing.

B. Method for Reducing Pore Size

The composition is also effective in reducing the size of Pores, as established in Example 7. The composition may be topically applied one or more times per day, either alone or in combination with other skin treatment products such as skin cleaners, toners, serums, and the like, using compositions like those set forth herein. The composition demonstrated improvement in the reduction of pore size by 32% after immediate application.

C. Method for Improving Appearance of Lines & Wrinkles

The composition is also effective in reducing the appearance of lines and wrinkles as evidenced by the clinical studies set forth in Example 8, when topically applied one or more times per day. The composition of the invention showed significant improvement in the appearance of lines and wrinkles after immediate application and after 2, 4, 6, and 8 hours when compared with the commercial product Estee Lauder Perfectionist CP+.

The invention will be further described in connection with the following examples which are set forth for the purpose of illustration only.

Example 1

A skin care composition in accordance with the invention was made as follows:

| Ingredient | % by weight |
|---|---|
| Water | QS100 |
| Glycerin (moisturizer) | 10.15 |
| Polyacrylate crosspolymer-7 (polymer) | 4.25 |
| Shea butter (moisturizer) | 3.18 |
| Vinyl dimethicone/methicone/silsesquioxane copolymer (silicone elastomer) | 3.00 |
| Hydroxyethyl urea (moisturizer) | 2.50 |
| Myristyl myristate (moisturizer) | 2.00 |
| Pentaerythrityl distearate (moisturizer) | 2.00 |
| Acetylated glycol stearate (moisturizer) | 1.00 |
| Sodium stearoyl glutamate (moisturizer) | 0.50 |
| Hydrogenated polyisobutene (moisturizer) | 0.38 |
| Hydrogeneted lecithin (moisturizer) | 0.30 |
| Adipic acid/neopentylglycol crosspolymer | 0.30 |
| Pentylene glycol (moisturizer) | 0.35 |
| Caprylyl glycol (preservative) | 0.35 |
| Alcaligenes polysaccharides (botanical extract) | 0.10 |
| Glucose (moisturizer) | 0.10 |
| Dimethicone (moisturizer) | 0.05 |
| Dipotassium EDTA (preservative) | 0.05 |
| Sodium hyaluronate (moisturizer) | 0.04 |
| Phenoxyethanol (preservative) | 0.04 |
| Squalane (moisturizer) | 0.03 |
| *Laminaria digitata* extract (botanical extract) | 0.02 |
| VP/VA copolymer (moisturizer) | 0.008 |
| Ceremide III (moisturizer) | 0.004 |
| Amodimethicone (moisturizer) | 0.003 |
| Hydroxypropyl methylcellulose | 0.003 |
| Sodium chloride | 0.001 |
| Chlorophenesin (preservative) | 0.0008 |
| Citric acid (preservative) | 0.0001 |
| Glucose oxidase (preservative) | 0.00008 |
| Lactoperoxidase (preservative) | 0.00008 |

The composition was prepared by separately combining the aqueous phase and oil phase ingredients, then mixing well to emulsify into an oil in water emulsion.

Example 2

Primer compositions for use under facial or eye makeup were prepared as follows:

| Ingredient | % by weight | | |
|---|---|---|---|
| WATER\AQUA\EAU | QS100 | QS100 | QS100 |
| GLYCERIN | 15.60 | 15.60 | 15.60 |
| METHYL PERFLUOROBUTYL ETHER | 10.00 | | 10.00 |
| PERFLUOROHEXANE | — | 8.15 | |
| PERFLUORODECALIN | | 1.05 | |
| PERFLUOROCYCLOMETHYL-PENTANE | | 0.80 | |
| IRON OXIDES | 10.22 | 0.28 | 0.11 |
| DIMETHICONE/VINYL DIMETHICONE CROSSPOLYMER | 3.95 | 3.95 | 3.95 |
| DIMETHICONE | 3.75 | 3.75 | 3.75 |
| *MANGIFERA INDICA* (MANGO) SEED BUTTER | 3.00 | 2.00 | 3.00 |
| POLYACRYLATE CROSSPOLYMER-7 | 2.99 | 2.99 | 2.99 |
| HYDROGENATED POLYISOBUTENE | 1.50 | 1.50 | 1.50 |
| HYDROGENATED LECITHIN | 1.20 | 1.20 | 1.20 |
| TITANIUM DIOXIDE (CI 77891) | 1.11 | 1.64 | 1.92 |
| PENTYLENE GLYCOL | 1.00 | 1.00 | 1.00 |
| *BUTYROSPERMUM PARKII* (SHEA BUTTER) | 0.70 | 0.70 | 0.70 |
| PEG-10 DIMETHICONE | 0.50 | 0.50 | 0.50 |
| GALACTOARABINAN | 0.32 | 0.05 | 0.05 |
| PHENOXYETHANOL | 0.28 | | 0.30 |
| SODIUM POLYACRYLATE STARCH | 0.15 | 0.15 | 0.15 |
| LAURETH-9 | 0.15 | 0.15 | 0.15 |
| LAURETH-23 | 0.10 | 0.10 | 0.10 |
| GLUCOSE | 0.10 | 0.10 | 0.10 |
| SQUALANE | 0.10 | 0.10 | |
| SODIUM BENZOATE | 0.03 | 0.03 | 0.03 |
| *LAMINARIA DIGITATA* EXTRACT | 0.02 | 0.02 | 0.02 |
| CERAMIDE 3 | 0.02 | 0.02 | 0.02 |
| CITRIC ACID | 0.01 | 0.005 | 0.005 |
| SODIUM CHLORIDE | | 0.001 | 0.001 |
| TOCOPHEROL | | 0.0005 | 0.0005 |
| CAPRYLYL GLYCOL | 0.10 | | |
| GLUCOSE OXIDASE | 0.00008 | | 0.0008 |

Compositions were prepared by combining ingredients and mixing well to form an emulsion.

Example 3

| Ingredients | % by weight | | | |
|---|---|---|---|---|
| | Stick | Cream | Lotion | Serum |
| Water | QS100 | QS100 | QS100 | QS100 |
| Glycerin | 10.00 | 15.00 | 16.33 | 15.00 |
| Acetylated glycol stearate | | 3.00 | | |
| Dimethicone/vinyl dimethicone crosspolymer | 8.10 | 1.72 | 2.22 | |
| Dimethicone | | 1.76 | 5.10 | 1.00 |
| Jojoba seed oil | | | 2.00 | |
| Polysilicone 22 | | | 2.00 | |
| Trehalose | | | 0.53 | |
| Dimethicone crosspolymer | | 0.20 | 0.20 | |
| Vinyl dimethicone/methyl silsesquioxane copolymer | | 3.00 | 3.00 | |
| Myristyl myristate | | 1.75 | | |
| Hydrogenated polyisobutene | | 0.15 | 0.30 | |
| Urea | | | 0.30 | |
| Hydrogenated lecithin | | 0.12 | 0.24 | |
| Shea butter | | 1.57 | 0.14 | |
| Mango seed butter | | 1.50 | | |
| Sodium stearoyl glutamate | | 0.50 | | |
| Silica | 4.08 | | | |
| HDI trimethylolhexyllactone crosspolymer | 3.92 | | | |
| Butylene glycol | 3.10 | | 2.55 | 2.00 |
| Caprylyl methicone | | | 3.00 | 2.00 |
| Sodium stearate | 2.50 | | | |
| Propanediol | 2.00 | | | |
| Bis-PEG methyl ether dimethylsilane | 2.00 | | | |
| Sorbitol | 0.70 | | 0.35 | 0.35 |
| Sodium PCA | | | 0.33 | |
| Lauryl PEG-9 polydimethyl siloxane | | | 0.50 | 0.30 |
| Phenoxyethanol | 0.60 | | 0.10 | 0.10 |
| *Hypnea musciformis* (Algae) extract | 0.52 | 0.76 | 0.26 | 0.26 |
| PEG-150 distearate | 0.50 | | | |
| Beeswax | | 0.06 | 0.08 | |
| Sodium hyaluronate | | 0.05 | 0.09 | 0.10 |
| Laureth-9 | 0.45 | 0.09 | 0.10 | |
| *Gellidiella acerosa* extract | 0.37 | 0.19 | 0.19 | 0.10 |
| Caprylyl glycol | 0.30 | | | |
| Laureth-23 | 0.30 | 0.06 | 0.06 | |
| Polyquaternium-41 | | | 0.03 | |
| Sodium citrate | 0.30 | | | |
| Caffeine | 0.20 | 0.20 | 0.20 | 0.20 |
| Glucose | | 0.10 | 0.10 | 0.10 |
| Pentylene glycol | | | 0.10 | 0.20 |
| Algae extract | | | 0.50 | 0.50 |
| Polyacrylate crosspolymer-7 | 0.10 | 4.23 | 4.23 | 4.23 |

-continued

| Ingredients | % by weight | | | |
|---|---|---|---|---|
| | Stick | Cream | Lotion | Serum |
| PEG-11 methyl ether dimethicone | | | 0.50 | 0.50 |
| Sucrose | | | | 0.50 |
| Sodium benzoate | 0.08 | 0.015 | | |
| *Matricaria* extract | | 0.007 | 0.007 | 0.001 |
| *Chamomile* extract | | | 0.007 | |
| Squalane | | 0.01 | 0.02 | |
| Disodium EDTA | 0.05 | | | |
| *Laminaria digitata* | | 0.02 | 0.02 | 0.02 |
| Silica | | 0.02 | 0.02 | |
| Silica silylate | | 0.02 | 0.02 | |
| Alicaligenes polysaccharide | 0.02 | 0.02 | 0.08 | 0.08 |
| Citric acid | 0.015 | 0.003 | | |
| Ceramide-3 | | 0.002 | 0.003 | |
| Sodium chloride | | 0.001 | | 0.001 |
| Preservatives | 0.10 | 0.10 | | 0.10 |

The compositions were prepared by combining the ingredients and mixing well to emulsify.

Example 4

The composition of Example 1 ("Formula 1") was tested against two commercial skin care products to determine water loss over time after application to skin.

Formula 2 was Clinique® Moisture Surge Extended Thirst Relief, a commercial product having an ingredient list as set forth below.
Water, cyclopentasiloxane, butylene glycol, glycerin, *Betula alba* (birch) bark extract, *Silybum marianum* (lady's thistle) extract, *Camellia sinensis* (green tea) leaf extract. *Saccharomyces lysate* extract, sucrose, Aloe barbadensis leaf water, trehalose, hydroxyethyl urea. *Thermus thermophillus* ferment, sorbitol, oleth-10, tromethamine, caffeine, hydrogenated lecithin, sodium hyaluronate, tocopheryl acetate, palmitoyl oligopeptide, caprylyl glycol, dimethicone, glyceryl polymethacrylate, PEG-8, ammonium acryloyldimethyltaurate/VP copolymer, magnesium ascorbyl phosphate, carbomer, hexylene glycol, disodium edta, phenoxyethanol, red 4 (ci 14700), yellow 5 (ci 19140).

Formula 3 was Estee Lauder [CP+] Targeted Deep Wrinkle Filler, a commercial product having an ingredient list as set forth below.
Cyclopentasiloxane, water, Polysilicone-11, dimethicone, HDI/trimethylol hexyllactone crosspolymer, silica, butylene glycol, yeast extract, *Scutellaria baicalensis* extract, *Morus nigra* (Mulberry) root extract, *Siegesbeckia orientalis* (St. Paul's Wort) extract, *Salvia sclarea* (Clary) extract, *Vitis vinifera* (Grape) fruit extract, *Hordeum vulgare* (Barley) extract, *Chamomilla recutita* (Matricaria) flower extract. *Triticum vulgare* (Wheat) germ extract, *Zea mays* (Corn) kernel extract, *Glycyrrhiza glabra* (Licorice) root extract, *Narcissus tazetta* bulb extract, *Boswellia serrata* extract, *Silybum marianum* (Lady's Thistle) extract, Fish (Pisces) collagen, Polysorbate 40, Ethylhexyl glycerin, Caffeine, Cholesterol, Hydrolyzed fish (Pisces) collagen, Pentylene glycol, Whey protein, Pantethine, Creatine, *Glycine soja* (Soybean) protein, glycerin, PEG-10 dimethicone. Sodium PCA, Ammonium Acryloyldimethyltaurate/VP copolymer, Linoleic acid, Glyceryl polymethacrylate, Polyquaternium-51, Squalan, Propylene glycol dicaprate, Acetyl carnitine HCL, Acetyl hexapeptide-8, Phytosphingosine, Sodium hyaluronate, Adenosin phosphate, Aminopropyl ascorbyl phosphate, PEG-8, Disodium distyrylbiphenyl disulfonate. Lecithin, Palmitoyl oligopeptide, Disodium NADH, Caprylyl glycol, Decarboxyl carnosine HCL, Laurdimonium hydroxypropyl hydrolyzed soy protein, Sodium beta-sitosteryl sulfate, fragrance, sodium chondroitan sulfate, tocopheryl acetate, hexylene glycol, hydroxyethylcellulose, sodium chloride, xanthan gum, disodium EDTA, phenoxyethanol, titanium dioxide (CI 77891), Mica.

A moisturizing test on Formulas 1, 2, and 3 was performed by weighing a 20 mg sample of each composition and applying it to a 1×1 inch area on the outer side of the test subject's forearm. A reading was taken at 1, 3, and 5 hours using a Nova Meter DPM9003 with a 1 cm. diameter probe. The results are as set forth in FIG. 1.

The composition of the invention provided significantly improved moisturization when compared to Formulas 2 and 3.

Example 5

Figure 2:
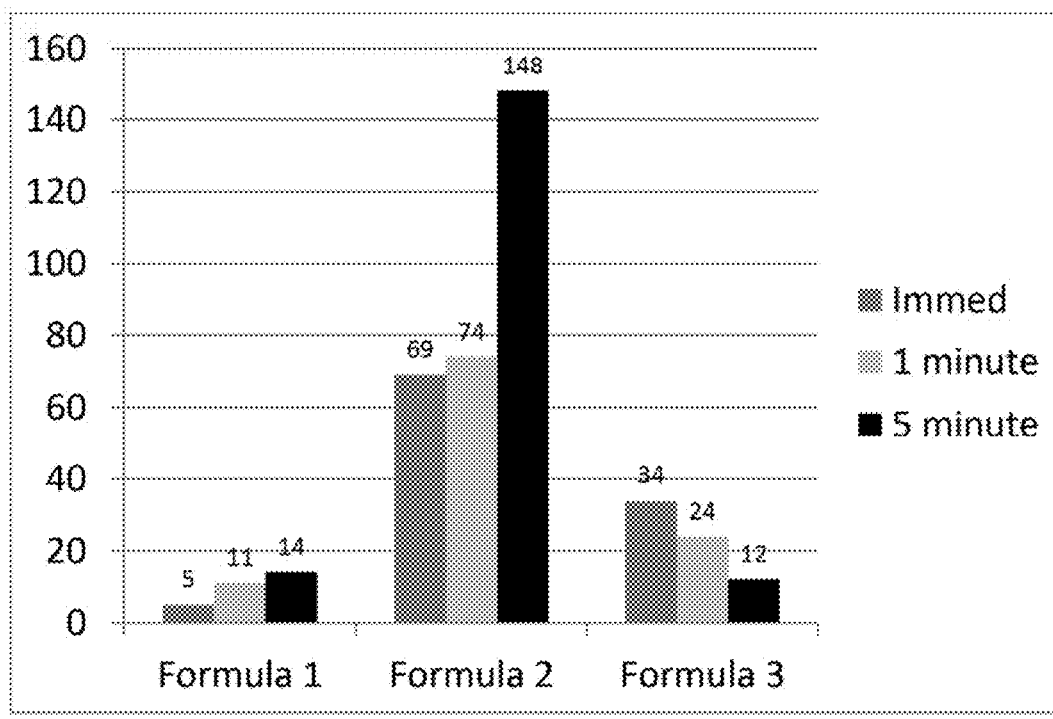
FIG. 2: shows that the composition of the invention (Formula 1) provides improved de-glossing when compared to test formulas (2 & 3).

Gloss was measured immediately, at 1 minute, and at 5 minutes by drawing 2 mil films of Formulas 1, 2, and 3 down on a microscopy slide (75×50×1 mm) using a Multiple Clearance Square Applicator (P.G.&T.Co. #3). Gloss of the film was measured using a BYK-Garner micro-TRI gloss meter. The results are as set forth in FIG. 2.

The gloss reading of Formula 1 of the invention was the lowest, thus illustrating the blurring effect of the composition on facial skin irregularities.

Example 6

The gloss of Polyacrylate crosspolymer-7 and Sodium polyacrylate were comparatively tested using the same procedure set forth in Example 3. The Sodium polyacrylate was purchased from Cognis Corporation under the Cosmedia SP trade name. Test samples were prepared as follows:

| Ingredient | Sample 1 | Sample 2 |
|---|---|---|
| DI water | 69.3 | 73.3 |
| Glyserin | 25 | 25 |
| Phenoxyethanol | 0.7 | 0.7 |
| Polyacrylate crosspolymer-7 | 5 | — |
| Sodium Polyacrylate* | — | 1 |

*Cosmedia SP Cognis Corporation

Gloss readings were measured immediately, and after 1 and 5 minutes with the gloss meter. The results are as follows:

| Sample | 60 degree gloss @ Immediate | 60 degree gloss @ 1 min | 60 degree gloss @ 5 min |
|---|---|---|---|
| 1 | 18.3 | 26.8 | 38.4 |
| 2 | 101 | 104 | 66.5 |

The above results demonstrate that Formula 1, the composition of the invention, is significantly less glossy when topically applied (e.g. improved de-glossing) than the comparative composition.

Example 7

A composition was prepared as follows:

| Ingredient | % by weight |
| --- | --- |
| Water | QS100 |
| Glycerin | 15.60 |
| Perfluorohexane | 8.15 |
| Dimethicone/vinyl dimethicone crosspolymer | 3.95 |
| Dimethicone | 3.75 |
| Polyacrylate crosspolymer-7 | 2.99 |
| *Mangifera indicia* seed butter | 2.00 |
| Hydrogenated polyisobutene | 1.50 |
| Hydrogenated lecithin | 1.20 |
| Perfluorodecalin | 1.05 |
| Pentylene glycol | 1.00 |
| Perfluoromethyl cyclopentane | 0.80 |
| Shea butter | 0.70 |
| PEG-10 dimethicone | 0.50 |
| Laureth-9 | 0.15 |
| Sodium polyacrylate starch | 0.15 |
| Laureth-23 | 0.10 |
| Caprylyl glycol | 0.10 |
| Squalane | 0.10 |
| Glucose | 0.10 |
| Sodium benzoate | 0.03 |
| *Laminaria digitata* extract | 0.02 |
| Ceramide-3 | 0.018 |
| Citric acid | 0.005 |
| Sodium chloride | 0.001 |
| Tocopherol | 0.0005 |
| Lactoperoxidase | 0.0008 |
| Glucose oxidase | 0.0008 |

The composition was prepared by combining the ingredients and mixing well to form an emulsion. The composition was tested on 25 adult women who had visible pores and had not been using retinoids or alpha hydroxy acid products in the previous 6 months or been subject to cosmetic procedures. The women were instructed to apply the composition one time when present at the testing facility.

The composition was tested on 25 female panelists between the ages of 20 and 63 years of age. The panelists were instructed to arrive at the test center with a clean face having no applied products. They were instructed to apply the above product to the face one time.

Digital Photography Via Canfield's VISIA-CR™ Facial Imaging

The efficacy of the applied product was determined by photographing the panelists after application of the product with the Canfield VISIA-CR™ facial imaging system to produce high resolution reproducible facial images to facilitate clinical evaluations of various skin features (*Canfield Scientific: Dermatologic Clinics:* 14, 713-721; 1996).

To evaluate the immediate reduction in the appearance of pores, photos were taken using the Canfield Visia-CR Facial Imaging System utilizing the standard lighting template which captured panelists' images as they would appear in normal daylight. Panelists' heads were placed in the head rest to ensure reproducibility of positioning. One standard photograph of the face was taken and analyzed using the Image Pro 6.0 image analysis program. The appearance of pores was assessed by be examining changes in area before and after product use. A decrease in the area represents a reduction in pore size. The results showed a 32% reduction in the size and appearance of pores among all panelists collectively after immediate application of the composition. Thus the composition of the invention has efficacy in reducing pore size.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

The invention claimed is:

1. A method for moisturizing a keratin surface and blurring the appearance of defects by de-glossing the keratin surface by topically applying to a keratin surface having defects and in need of moisturization, a copolymer of methacrylate PPG-6 phosphate and one or more monomers of acrylic acid, methacrylic acid or one of their simple esters, crosslinked with dimethicone PEG/PPG-25/29 acrylate in a cosmetically acceptable composition, wherein the composition containing the copolymer provides improved moisturization and blurring of skin defects when compared to the same composition not containing the copolymer.

2. The method of claim 1 wherein the keratin surface is skin or hair.

3. The method of claim 1 wherein the keratin surface is facial skin.

4. The method of claim 1 wherein the composition contains at least one additional moisturizer that improves moisturization of the composition and improves or maintains the same de-glossing when compared to the composition not containing the additional moisturizer.

5. The method of claim 1 wherein the composition further comprises at least one botanical extract.

6. The method of claim 1 wherein the composition is applied to skin once or twice per day.

7. The method of claim 1 wherein the composition is in the form of a skin cream, lotion, beauty balm, foundation, or concealer.

8. The method of claim 7 wherein the composition is in the form of a skin cream.

9. A method for reducing the size of pores on skin by topically applying to a skin surface having enlarged pores a copolymer of methacrylate PPG-6 phosphate and one or more monomers of acrylic acid, methacrylic acid or one of their simple esters, crosslinked with dimethicone PEG/PPG-25/29 acrylate in a cosmetically acceptable composition wherein the composition-containing the polymer reduces the size of skin pores when compared to the same composition not containing the copolymer.

10. A method for reducing the appearance of lines and wrinkles on skin by topically applying a copolymer of methacrylate PPG-6 phosphate and one or more monomers of acrylic acid, methacrylic acid or one of their simple esters, crosslinked with dimethicone PEG/PPG-25/29 acrylate in a cosmetically acceptable composition to skin having lines and wrinkles in need of improvement.

11. A method for treating skin to provide at least two benefits selected from the group: (a) moisturizing, (b) blurring the appearance of skin defects, (c) reducing pore size, (d) improving the appearance of dark under eye circles, (e) reducing skin redness, (f) minimizing the appearance of lines and wrinkles, (g) evening skin tone, (h) filling skin depressions, (i) hiding scars, (j) smoothing cellulite or "cottage cheese" skin, (k) reducing the ashy appearance of ethnic skin, (l) minimizing the appearance of irregularities and age spots on hands, face, and neck, (m) improving appearance of uneven pigmentation, (n) correcting color; and combinations thereof by applying a copolymer of methacrylate PPG-6 phosphate and one or more monomers of acrylic acid, methacrylic acid or one of their simple esters, crosslinked with dimethicone PEG/PPG-25/29 acrylate in a cosmetically acceptable composition to skin in need of improvement in two or more of the benefits selected.

12. A method for blurring the appearance of defects on a keratin surface by de-glossing the keratin surface, by topically applying to a keratin surface having defects a copolymer of methacrylate PPG-6 phosphate and one or more monomers of acrylic acid, methacrylic acid or one of their simple esters, crosslinked with dimethicone PEG/PPG-25/29 acrylate in a cosmetically acceptable composition, wherein the composition containing the copolymer exhibits improved blurring of skin defects when compared to the same composition not containing the copolymer.

* * * * *